US009095549B2

(12) United States Patent
Joubert et al.

(10) Patent No.: US 9,095,549 B2
(45) Date of Patent: Aug. 4, 2015

(54) DIAGNOSIS AND PROGNOSIS OF COLORECTAL CANCER

(75) Inventors: Richard Joubert, Hofheim am Taunus (DE); Petra Prefot, Wiesbaden (DE); Gitte Boehm, Frankfurt am Main (DE); Juergen Arnhold, Rettert (DE); Claudia Hoehle, Liederbach (DE); Erhard Neukum, Koenigstein im Taunus (DE); Juergen Schaefer, Lauterbach (DE)

(73) Assignee: ELECTROPHORETICS LIMITED, Cobham Surrey (GB)

( * ) Notice: Subject to any disclaimer, the term of this patent is extended or adjusted under 35 U.S.C. 154(b) by 568 days.

(21) Appl. No.: 12/097,703

(22) PCT Filed: Dec. 15, 2006

(86) PCT No.: PCT/GB2006/050460
§ 371 (c)(1),
(2), (4) Date: Dec. 3, 2008

(87) PCT Pub. No.: WO2007/068985
PCT Pub. Date: Jun. 21, 2007

(65) Prior Publication Data
US 2009/0226905 A1    Sep. 10, 2009

(30) Foreign Application Priority Data

Dec. 16, 2005 (GB) .................................. 0525644.1
Jan. 30, 2006 (GB) .................................. 0601726.3

(51) Int. Cl.
G01N 33/53 (2006.01)
A61K 38/17 (2006.01)
G01N 33/574 (2006.01)

(52) U.S. Cl.
CPC .......... *A61K 38/17* (2013.01); *G01N 33/57419* (2013.01)

(58) Field of Classification Search
None
See application file for complete search history.

(56) References Cited

U.S. PATENT DOCUMENTS

2004/0265230 A1* 12/2004 Martinez et al. ............. 424/1.49
2005/0260177 A1   11/2005 Xu et al.
2006/0029956 A1*  2/2006 Beyer et al. ................. 435/6

FOREIGN PATENT DOCUMENTS

WO    WO 03/089935     10/2003
WO    WO 2004/090550  * 10/2004

OTHER PUBLICATIONS

NCBI, "Q9NWR7" p. 1-2, printed Sep. 28, 2010.*
Tockman et al (Cancer Res., 1992, 52:2711s-2718s).*
Buckhaults et al (Cancer Research, 2001, 61:6996-7001).*
Cen et al (World J Gastroenterol 2004, 10:3122-3126).*
Chung et al (J of National Cancer Institute, 2003, 95:1624-1633).*
Greenbaum et al (Bioinformatics, 2002, 18:585-596).*
Shankavarum et al (Mol Cancer Ther, 2007, 6:820-832).*
Lu et al (Nature Biotechnology, Jan. 2007, 25:117-124).*
Pedersen et al, Labmedicine, Oct. 2011, 42:623-628.*
Wang et al (Lin Chuang Er Bi Hou Ke Za Zhi, Jul. 2001, 15:306-308, abstract ONLY).*
Zhong et al (Proteomics, 2004, 4:1216-1225, published online Feb. 2, 2004).*
Goransson et al (European Journal of Surgical Oncology).*
Hugo Gene Nomenclature Committee "SERPING1" printed Mar. 2013.*
Ahmed et al I (Proteomics 2005, 5:4625-4636).*
iHOP website, synonyms for "transferrin," printed Feb. 2014.*
Alfonso et al (Proteomics, 2005, 5:2602-2611).*
Ahmed et al II (British Journal of Cancer, 2004, 91:129-140).*
Etzioni et al (Nature Reviews, Apr. 2003, 3: internet pp. 1-10).*
Mercer (Immunol Ser, 1990, 53:39-54).*
Wang et al (Proteomics, 2004, 4:2476-2495).*
Luborsky et al (American Journal of Reproductive Immunology, 2005; 54:55-62).*
Taylor et al (Oncology Reports, 1998, 5:1519-1524).*
Wulfkuhle et al (New Trends in Cancer for the 21st Century, 2003, p. 59-68).*
Stulik et al (Electrophoresis, 2001, 22:3019-3025).*

(Continued)

*Primary Examiner* — Laura B Goddard
(74) *Attorney, Agent, or Firm* — Arent Fox LLP

(57) ABSTRACT

The invention relates to a method of diagnosis of colorectal cancer in a diagnostic sample of a valid body tissue taken from a human subject, which comprises detecting an increased concentration of a protein in the diagnostic sample, compared with a control, normal human sample, the protein being: transforming growth factor-beta induced protein IG-H3 (SwissProt Acc. No. Q15582); suppressor of G2 allele of SKP1 homolog (isoform 2) (SwissProt Acc. No. Q9Y2Z0-2); hypothetical protein (part of URG4) (SwissProt Acc. No. Q9NWR7); calponin-2 (SwissProt Acc. No. Q99439); heat shock protein HSP90-beta (SwissProt Acc. No. P08238); phosphoglycerate mutase 1 (SwissProt Acc. No. P18669); serpin C1 protein (SwissProt Acc. No. P01008); or haptoglobin precursor (SwissProt Acc. No. P00738); or a decreased concentration of a protein in the diagnostic sample, compared with a control, normal human sample, the protein being serotransferrin (SwissProt Acc. No. P02787); 26S proteasome subunit p40.5 (Swiss Prot Acc. No. Q9UNM7); aldo-keto reductase family 1 member B10 (SwissProt Acc. No. O60218); fructosamine-3-kinase (SwissProt Acc. No. Q9H479); peripherin (SwissProt Acc. No. P41219); alpha-2-macroglobulin (SwissProt Acc. No. P01023); serpin C1 protein (SwissProt Acc. No. P01008); or apolipoprotein A IV (SwissProt Acc. No. P06727). The same proteins can be used for prognosis by detecting changes in their concentration in the course of treatment for colorectal cancer.

28 Claims, 18 Drawing Sheets

(56) References Cited

OTHER PUBLICATIONS

Seibert et al (Briefings in Functional Genomics and Proteomics, May 2005, 4:16-26).*
Espina et al (Expert Opin. Biol. Ther. 2004, 4:83-93).*
Friedman et al (Proteomics, 2004, 4:793-811).*
Imafuku et al (Disease Markers, 2004, 20:149-153).*
Anderson et al (Journal of Proteome Research, 2005, 4:1123-1133).*
Nam et al (Proteomics, 2003, 3:2108-2115).*
Luo et al (British Journal of Cancer, 2002, 87:339-343).*
Roessler et al (Clinical Cancer Research, Sep. 15, 2005, 11:6550-6557).*
Goransson et al (European Journal of Surgical Oncology, 1996, 22:607-617).*
Ahmed, Farid; "Molecular Markers that Predict Response to Colon Cancer Therapy"; Expert Review of Molecular Design; vol. 5, No. 3, pp. 353-375; 2005.
Alaiya A. A. et al.; "Protein Expression Profiling in Human Lung, Breast, Bladder, Renal, Colorectal and Ovarian Cancers"; Journal of Chromatography B: Biomedical Sciences & Applications, Elsevier, Amsterdam, NL, vol. 787, No. 1; pp. 207-222; Apr. 5, 2003.
Albrethsen et al.; "Upregulated Expression of Human Neutrophil Peptide 1, 2 and 3 (HNP 1-3) in Colon Cancer Serum and Tumours; a Biomarker Study"; BMC Cancer; pp. 1-10; 2005.
Alessandro et al.; "Proteomic Approaches in Colon Cancer: Promising Tools for New Cancer Markers and Drug Target Discovery"; Critical Colorectal Cancer; vol. 4, No. 6, pp. 369-402; 2005.
Alfonso et al.; "Proteomic Expression Analysis of Colorectal Cancer by Two-Dimensional Differential Get Electrophoresis"; Proteomics Journal; vol. 5, pp. 2602-2611; 2005.
Bresalier et al.; "A Circulating Ligand for Galectin-3 is a Haptoglobin-Related Glycoprotein Elevated in Individuals with Colon Cancer"; Gastroenterology 2004, vol. 127; pp. 741-748.
Broll et al.; "Vascular Endothelia Growth Factor (VEGF)—A Valuable Serum Tumour Marker in Patients with Colorectal Cancer?"; European Journal of Surgical Oncology; vol. 27; pp. 37-42.
Buckhaults et al.; "Secreted and Cell Surface Genes Expressed in Benign and Malignant Colorectal Tumors"; Cancer Research; vol. 61; pp. 6996-7001; Oct. 1, 2001.
Drew at al.; "A Protemics Approach to Identify Changes in Protein Profiles in Pre-Cancerous Colon"; Biochemical and Biophysical Research Communications; vol. 330; pp. 81-87; 2005.
Du et al.; "a2-Marcroglobulin Attenuates b-Amyloid Peptide 1-40 Fibril Formation and Associated Neurotoxicity of Cultured Fetal Rat Cortical Neurons"; Journal of Neurochemistry; vol. 70; pp. 1182-1188; 1998.
Engwegen et al.; "Identification of Serum Proteins Discriminating Colorectal Cancer Patients and Healthy Controls Using Surface-Enhanced Laser Desorption Ionisation-Time of Flight Mass Spectrometry"; World Journal of Gastroenterology; vo. 12, No. 10; pp. 1536-1544; Mar. 14, 2006.
Escribano et al.; "cDNA from Human Oscular Ciliary Epithelium Homologous to Big-h3 is Preferentially Expressed as an Extracellular Protein in the Corneal Epithlium"; Journal of Cellular Physiology; vol. 160, pp. 511-521; 1994.
Evans et al.; "Target Discovery in Small-Molecule Cell-Based Screens by in situ Proteome Reactivity Profiling"; Nature Biotechnology; vol. 23, No. 10, pp. 1303-1307; Oct. 2005.
Fernadez-Fernandez et al.; "Significance of CA 72-4 in Colorectal Carcinoma. Comparison with CEA and CA 19-9"; European Journal of Surgical Oncology; vol. 21, pp. 388-390; 1995.
Friedman et al.; "Proteome Analysis of Human Colon Cancer by Two-Dimensional Difference Gel Electrophoresis and Mass Spectrometry"; Proteomics Journal; vol. 4, pp. 793-811; 2004.
Gold et al.; "Demonstration of Tumor-Specific Antigens in Human Colonic Carcinomata by Immunological Tolerance and Absorption Techniques"; The Journal of Experimental Medicine; vol. 121, pp. 439-462.
Hammel et al.; "Le Dosage Serique Des Anticorps Anti-p53: Application au Cancer Colorectal"; Rev Med Interne; vol. 21, pp. 167-173; 2000.

Kawakami et al.; "Proteomic Analysis of Sera from Hepatocellular Carcinoma Patients after Radiofrequency Ablation Treatment"; Proteomics Journal; vol. 5, pp. 4287-4295; 2005.
Kitching et al.; "Coordinate Gene Expression Patterns During Osteoblast Maturation and Retinoic Acid Treatment of MC3T3-E1 Cells"; Journal of Bone and Mineral Metabolism; vol. 20, pp. 269-280; 2002.
Lawrie et al.; "Application of Laser Capture Microdissection and Proteomics in Colon Cancer"; Journal of Clinical Pathology: Molecular Pathology; vol. 54, pp. 253-258; 2001.
Lilja et al.; "Prostate-Specific Antigen in Serum Occurs Predominantly in Complex with a1-Antichymotrypsin"; Clinical Chemistry; vol. 37, No. 9, pp. 1618-1625; 1991.
Moll et al.; "The Catalog of Human Cytokeratins: Patterns of Expression in Normal Epithelia, Tumors and Cultured Cells"; Cell; vol. 31, pp. 11-24; Nov. 1982.
Mori et al.; "Two-Dimensional Electrophoresis Database of Fluorescence-Labeled Proteins of Colon Cancer Cells"; Journal of Chromatography B; vol. 823, pp. 82-97; 2005.
Nikura et al.; "Identification of a Novel Splice Varian: Human SGT1B"; DNA Sequence; vol. 14, No. 6, pp. 463-441; Dec. 2003.
Nilsson et al.; "Sensitivity and Specificity of CA242 in Gastro-Intestinal Cancer. A comparison with CEA, CA50 and CA19-9"; Br. J. Cancer; vol. 65, pp. 2154-221; 1992.
Satiroglu et al.; "Hepatitis Bx Antigen Stimulates Expression of a Novel Cellular Gene, URG4, that Promotes Hepatocellular Growth and Survival"; Neoplasia; vol. 4, No. 4, pp. 355-368; 2002.
Shiota et al.; "Circulating p53 Antibody in Patients with Colorectal Cancer"; Digestive Diseases and Sciences; vol. 45, No. 1, pp. 122-128; Jan. 2000.
Sierko et al.: "Expression of Blood Coagulation Inhibitors in Color Cancer"; Pol. Merk. Lek.; vol. XX, No. 118; pp. 462-467; 2006.
Skonier J. et al.,; "CDNA Cloning and Sequence Analysis of Betaig-H3, A Novel Gene Induced in a Human Adenocarcinoma Cell Line After Treatment With Transforming Growth Factor-Beta"; DNA and Cell Biology, New York, New York; vol. 11, No. 7, pp. 511-522; Sep. 1992.
Rodriquez-Pineiro et al.; "Differential Expression of Serum Clusterin Isoforms in Colorectal Cancer"; Molecular & Cellular Proteomics; vol. 5, No. 9; pp. 1647-1657.
Roessler et al.; "Identification of PSME3 as a Novel Serum Tumor Marker for Colorectal Cancer by Combining Two-Dimensional Polyacrylamide Gel Electrophoresis with a Strictly Mass Spectrometry-based Approach for Data Analysis"; Molecular & Cellular Proteomics; vol. 5, No. 11; pp. 2092-2101.
Ward et al.; "Identification of Serum Biomarkers for Colon Cancer by Proteomic Analysis"; British Journal of Cancer; vol. 94; pp. 1898-1905; 2006.
Whitesell et al.; "HSP9 and the Chaperoning of Cancer"; Nature Review, Cancer; vol. 5, pp. 761-772; 2005.
Yamaguchi et al.; "Novel Serum Tumor Marker, RCAS1, in Pancreatic Diseases"; World Journal of Gastroenterology; vol. 11, No. 33, pp. 5199-5202; 2005.
Zervos et al.; "Differential Gene Expression in Patients Genetically Predisposed to Pancreatic Cancer"; Journal of Surgical Research; vol. 135, pp. 317-322; 2006.
D. Greenbaum, et al., "Comparing protein abundance and mRNA expression levels on a genomic scale", Genome Biology, vol. 4,.Issue 9, Article 117, Aug. 29, 2003, pp. 117-117.8.
Albrethsen, J. et al., "Upregulated expression of human neutrophil peptides 1, 2 and 3 (HNP 1-3) in colon cancer serum and tumours: a biomarker study", BMC Cancer 2005: vol. 5, Jan. 2005, pp. 8-17.
Hendrickson, E.R. et al., "High sensitivity multianalyte immunoassay using covalent DNA-labeled antibodies and polymerase chain reaction", Nucleic Acids Research, vol. 23, No. 3, 1995, pp. 522-529.
Zhang, L. et al., "Gene Expression Profiles in Normal and Cancer Cells", Science, vol. 276, May 23, 1997, pp. 1268-1272.
Tufan, N et al., "Hepatitis Bx Antigen Stimulates Expression of a Novel Cellular Gene, URG4, that Promotes Hepatocellular Growth and Survival", Neoplasia, vol. 4, No. 4, 2002, pp. 355-368.

* cited by examiner

| Gel name | Number of spots detected in gel | Sum of volume (IOD) of all detected spots | Scaling factor (Sum IOD_Ref_Gel / Sum_IOD_Gels) |
|---|---|---|---|
| n-03-0077_2201 | 1170 | 268936 | 0,699 |
| n_03-0083_2203 | 1116 | 273562 | 0,687 |
| n_03-0089_2205 | 1121 | 293667 | 0,640 |
| n_03-0112_2207 | 1161 | 241576 | 0,778 |
| n_03-0271_2209 | 857 | 200360 | 0,938 |
| n_03-0368_2211 | 1173 | 242881 | 0,774 |
| n_03-0504_2215 | 1130 | 187285 | 1,004 |
| *n_03-0562_2217* | *1255* | *187958* | *1,000* |
| n_03-0633_2219 | 1173 | 204660 | 0,919 |
| n_04-0719_2221 | 1380 | 276484 | 0,680 |
| n_04-0740_2223 | 950 | 190246 | 0,988 |
| n_04-0798_2225 | 928 | 172756 | 1,088 |
| n_04-0885_2227 | 1176 | 211831 | 0,887 |
| n_04-0933_2229 | 1184 | 210077 | 0,895 |
| t_03-0077_2202 | 1190 | 195080 | 0,964 |
| t_03-0083_2204 | 1130 | 224935 | 0,836 |
| t_03-0089_2206 | 1061 | 176054 | 1,068 |
| t_03-0112_2208 | 1090 | 222556 | 0,845 |
| t_03-0271_2210 | 1070 | 286487 | 0,656 |
| t_03-0368_2212 | 1391 | 252213 | 0,745 |
| t_03-0393_2214 | 1342 | 239049 | 0,786 |
| t_03-0562_2218 | 1236 | 183045 | 1,027 |
| t_04-0719_2222 | 1094 | 205622 | 0,914 |
| t_04-0740_2224 | 1398 | 233854 | 0,804 |
| t_04-0798_2226 | 1259 | 243293 | 0,773 |
| t_04-0885_2228 | 1345 | 279073 | 0,674 |
| t_04-0933_2230 | 1182 | 210016 | 0,895 |

FIGURE 1: For each gel, number of detected spots, the sum of volume (IOD) of all spots and the scaling factor (S.F.) are indicated. The gel in italic corresponds to the Reference gel.

| Spot no.[a] | Protein name | Acc. No.[b] | Norm. Vol Control | CV (%) | Norm. Vol Disease | CV (%) | Expression ratio[c] | T-test (p)[d] | Mann-Whitney Test | Detection ratio[e] | Theoretical Mr | pI | Cover-age (%) | Peptide matched |
|---|---|---|---|---|---|---|---|---|---|---|---|---|---|---|
| 241 | Glycyl-tRNA synthetase | P41250 | 0,0690 | 61 | 0,1413 | 46 | 2,05 | 0,004 | 0,007 | 13/12 | 84649 | 7,85 | 24% | 13 |
| 407 | Transforming growth factor-beta induced protein IG-H3 | Q15582 | 0,4939 | 59 | 1,0262 | 45 | 2,08 | 0,002 | 0,005 | 14/13 | 74681 | 7,62 | 33% | 14 |
| 503 | 60 kDa heat shock protein, mitochondrial | P10809 | 0,5618 | 40 | 1,3908 | 35 | 2,48 | 0,000 | 0,000 | 14/13 | 61213 | 5,70 | 37% | 17 |
| 733 | Serum albumin | P02768 | 0,7249 | 57 | 1,7087 | 50 | 2,36 | 0,001 | 0,000 | 14/13 | 71705 | 6,42 | 22% | 13 |
| 768 | Adenosylhomocysteinase | P23526 | 0,3876 | 56 | 0,8449 | 47 | 2,18 | 0,002 | 0,002 | 14/13 | 47585 | 5,92 | 27% | 12 |
| 949 | Suppressor of G2 allele of SKP1 homolog (Isoform 2) | Q9Y2Z0-2 | 0,0611 | 81 | 0,2888 | 67 | 4,73 | 0,001 | 0,001 | 12/13 | 37805 | 5,11 | 18% | 5 |
| 975 | Hypothetical protein (part of URG4) | Q9NVR7 | 0,0904 | 88 | 0,2899 | 77 | 3,21 | 0,011 | 0,004 | 12/12 | 37011 | 7,73 | 23% | 5 |
| 983 | Calponin-2 | Q99439 | 0,3706 | 68 | 0,9562 | 50 | 2,58 | 0,001 | 0,004 | 12/13 | 33566 | 6,92 | 35% | 13 |
| 1015 | Inorganic pyrophosphatase | Q15181 | 0,6728 | 40 | 1,6838 | 54 | 2,50 | 0,002 | 0,000 | 14/13 | 32660 | 5,54 | 52% | 11 |
| 1049 | Annexin A4 | P09525 | 1,0053 | 48 | 2,1012 | 42 | 2,09 | 0,001 | 0,001 | 14/13 | 36115 | 5,84 | 62% | 20 |
| 1052 | F-actin capping protein beta subunit isoform 2 | P47756-2 | 0,7849 | 41 | 1,6278 | 63 | 2,07 | 0,013 | 0,004 | 14/13 | 33781 | 6,01 | 41% | 13 |
| 1081 | Tropomyosin alpha 4 chain isoform 1 | P67936-1 | 1,1844 | 61 | 2,6445 | 41 | 2,23 | 0,001 | 0,001 | 14/13 | 28522 | 4,67 | 59% | 15 |
| 1171 | Rho GDP-dissociation inhibitor 1 | P52565 | 0,3874 | 43 | 0,8742 | 52 | 2,26 | 0,003 | 0,000 | 12/13 | 23207 | 5,02 | 28% | 7 |
| 1171 | 14-3-3 protein beta/alpha | P31946 | 0,3874 | 43 | 0,8742 | 52 | 2,26 | 0,003 | 0,000 | 12/13 | 27951 | 4,76 | 25% | 6 |
| 1191 | Heat shock protein HSP90-beta (protein fragment) | P08238 | 1,5802 | 32 | 3,3043 | 46 | 2,09 | 0,001 | 0,000 | 14/13 | 83133 | 4,97 | 16% | 15 |
| 1229 | Translationally controlled tumor protein | P13693 | 1,0493 | 53 | 2,4333 | 35 | 2,32 | 0,000 | 0,000 | 14/13 | 19596 | 4,84 | 31% | 7 |
| 346 | Serum albumin | P02768 | 0,7676 | 47 | 0,2419 | 33 | 0,32 | 0,000 | 0,001 | 14/12 | 71705 | 6,42 | 43% | 19 |
| 361 | Serotransferrin | P02787 | 0,4779 | 87 | 0,0766 | 80 | 0,16 | 0,003 | 0,001 | 14/13 | 77050 | 6,81 | 27% | 19 |
| 364 | Serum albumin | P02768 | 1,3826 | 42 | 0,6220 | 55 | 0,45 | 0,001 | 0,001 | 14/11 | 71705 | 6,42 | 41% | 19 |
| 404 | Serum albumin | P02768 | 1,3826 | 62 | 0,3212 | 45 | 0,23 | 0,000 | 0,000 | 14/13 | 71705 | 6,42 | 40% | 20 |
| 435 | Serum albumin | P02768 | 1,3777 | 59 | 0,2378 | 60 | 0,17 | 0,000 | 0,000 | 14/10 | 71705 | 6,42 | 37% | 19 |
| 460 | Serum albumin | P02768 | 1,6564 | 79 | 0,4633 | 129 | 0,28 | 0,006 | 0,000 | 14/13 | 71705 | 6,42 | 33% | 15 |
| 462 | Serum albumin | P02768 | 2,4347 | 54 | 0,8209 | 90 | 0,34 | 0,001 | 0,000 | 14/13 | 71705 | 6,42 | 38% | 18 |
| 519 | Serum albumin | P02768 | 0,3281 | 58 | 0,1314 | 77 | 0,40 | 0,004 | 0,001 | 14/10 | 71705 | 6,42 | 29% | 12 |
| 877 | Serum albumin | P02768 | 2,9124 | 34 | 1,0186 | 90 | 0,35 | 0,000 | 0,000 | 14/12 | 71705 | 6,42 | 28% | 15 |
| 877 | 26S proteasome subunit p40.5 [Fragment] | Q9UNM7 | 2,9124 | 34 | 1,0186 | 90 | 0,35 | 0,000 | 0,000 | 14/12 | 39871 | 5,90 | 28% | 8 |
| 943 | Aldo-keto reductase family 1 member B10 | O60218 | 0,7774 | 42 | 0,3535 | 73 | 0,46 | 0,002 | 0,003 | 14/11 | 36021 | 7,12 | 45% | 10 |
| 943 | Fructosamine-3-kinase | Q9H479 | 0,7774 | 42 | 0,3535 | 73 | 0,46 | 0,002 | 0,003 | 14/11 | 35571 | 7,13 | 22% | 7 |
| 1060 | Serum albumin | P02768 | 1,6421 | 60 | 0,3985 | 112 | 0,24 | 0,000 | 0,000 | 14/13 | 71705 | 6,42 | 33% | 22 |
| 1256 | Serum albumin | P02768 | 1,1514 | 87 | 0,2362 | 115 | 0,21 | 0,005 | 0,000 | 14/12 | 71705 | 6,42 | 30% | 16 |
| 543 | Peripherin | P41219 | 0,1779 | 57 | | | predom in conti | | | 14/0 | 53878 | 5,43 | 48% | 19 |
| 1354 | Phosphoglycerate mutase 1 | P18669 | 0,2465 | 131 | 0,3072 | 148 | predom in test | 0,250 | 0,333 | 2/10 | 28673 | 6,75 | 37% | 8 |
| 1458 | Tropomyosin alpha 4 chain isoform 1 | P67936-1 | | - | 0,2004 | 105 | predom in test | 0,843 | 0,909 | 1/9 | 28522 | 4,67 | 38% | 6 |
| 543 left | 60 kDa heat shock protein, mitochondrial | P10809 | 0,0570 | | 0,2230 | 14 | predom in test | | | 0/13 | 61213 | 5,70 | 33% | 16 | a) Spot number correspond to spot number in Reference gel from Progenesis
b) Accession Number from Swiss-Prot Database
c) Mean normalised spot volume in the disease sample divided by that in control sample
d) Significance (p) value for the difference in normalised spot volumes (expression ration) compared by Student's t-test
e) Number of gel from the control group within the spot was detected / Number of gels from the disease group within the equivalent spot was detected
CV means coefficient of variation FIGURE 2: Differentially expressed protein spots after image analysis of tumour vs. normal colorectal tissues and identified by PMF.

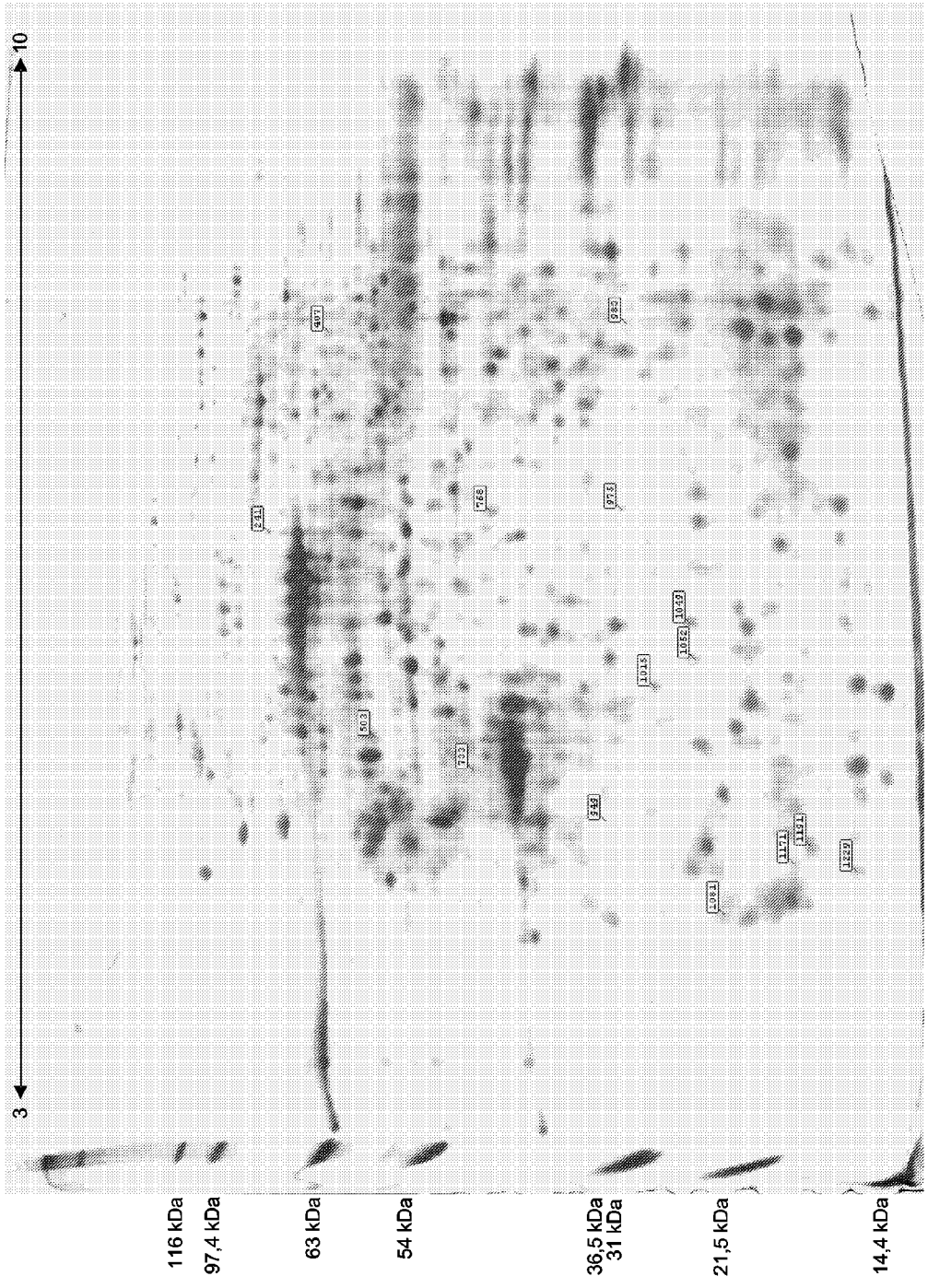
FIGURE 3: 2-D profile of proteins extracted from tumour tissue. The pattern shown corresponds to a 2-D PAGE image of silver-stained gel. Spot numbers indicated protein spots up regulated in tumour tissue.

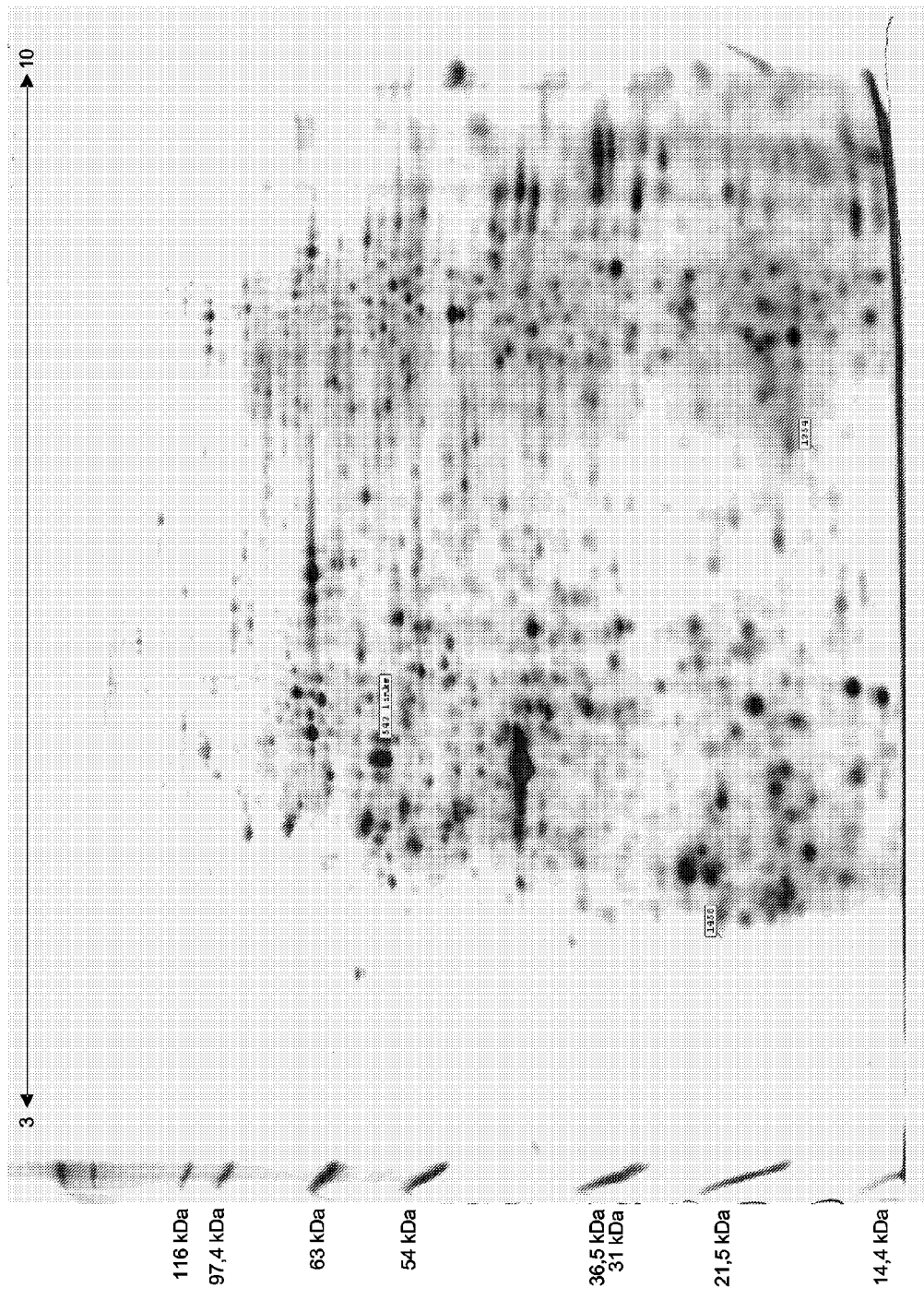
FIGURE 4: 2-D profile of proteins extracted from tumour tissue. The pattern shown corresponds to a 2-D PAGE image of silver-stained gel. Spot numbers indicated protein spots predominant in tumour tissue.

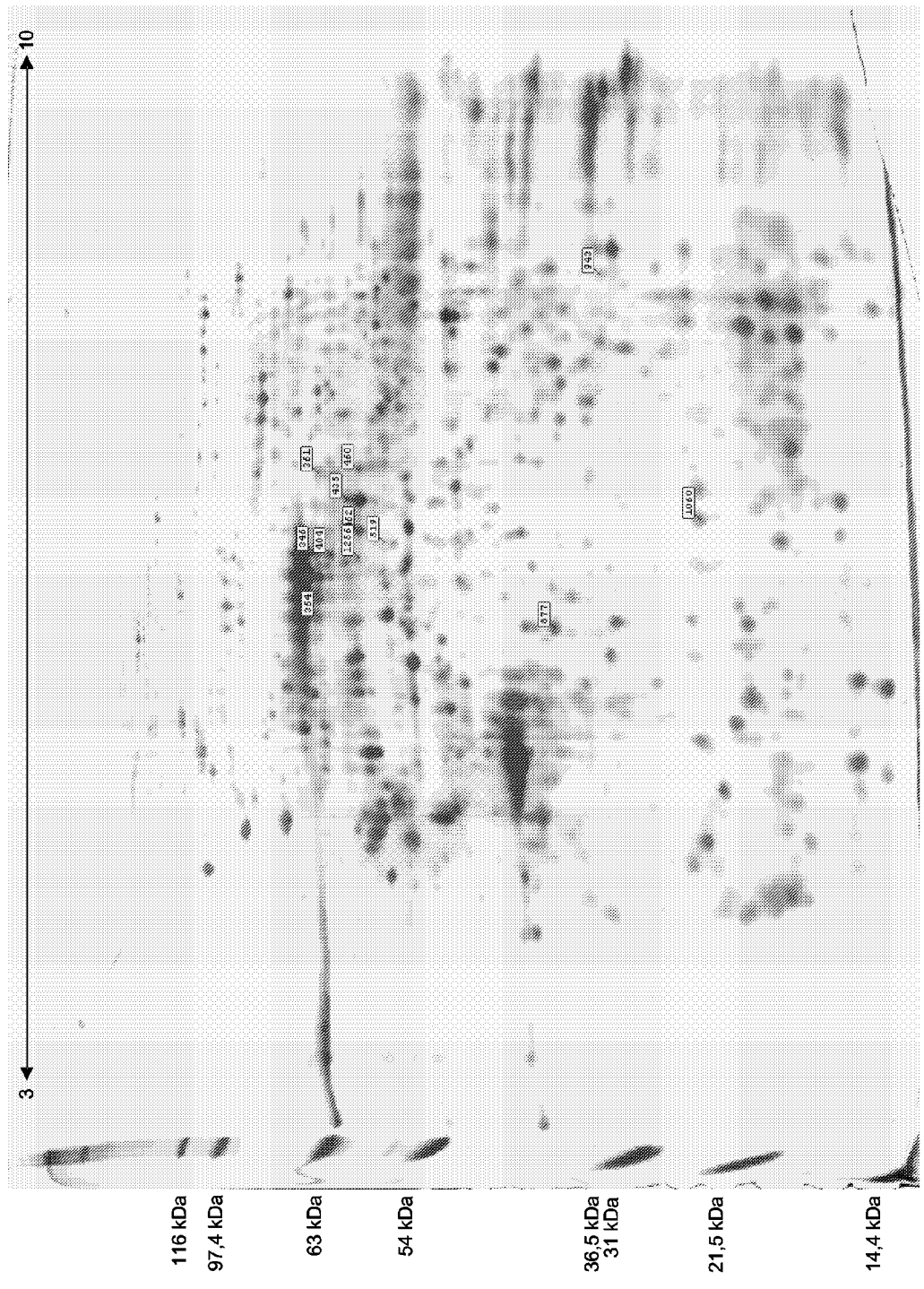
FIGURE 5: 2-D profile of proteins extracted from tumour tissue. The pattern shown corresponds to a 2-D PAGE image of silver-stained gel. Spot numbers indicated protein spots down regulated in tumour tissue.

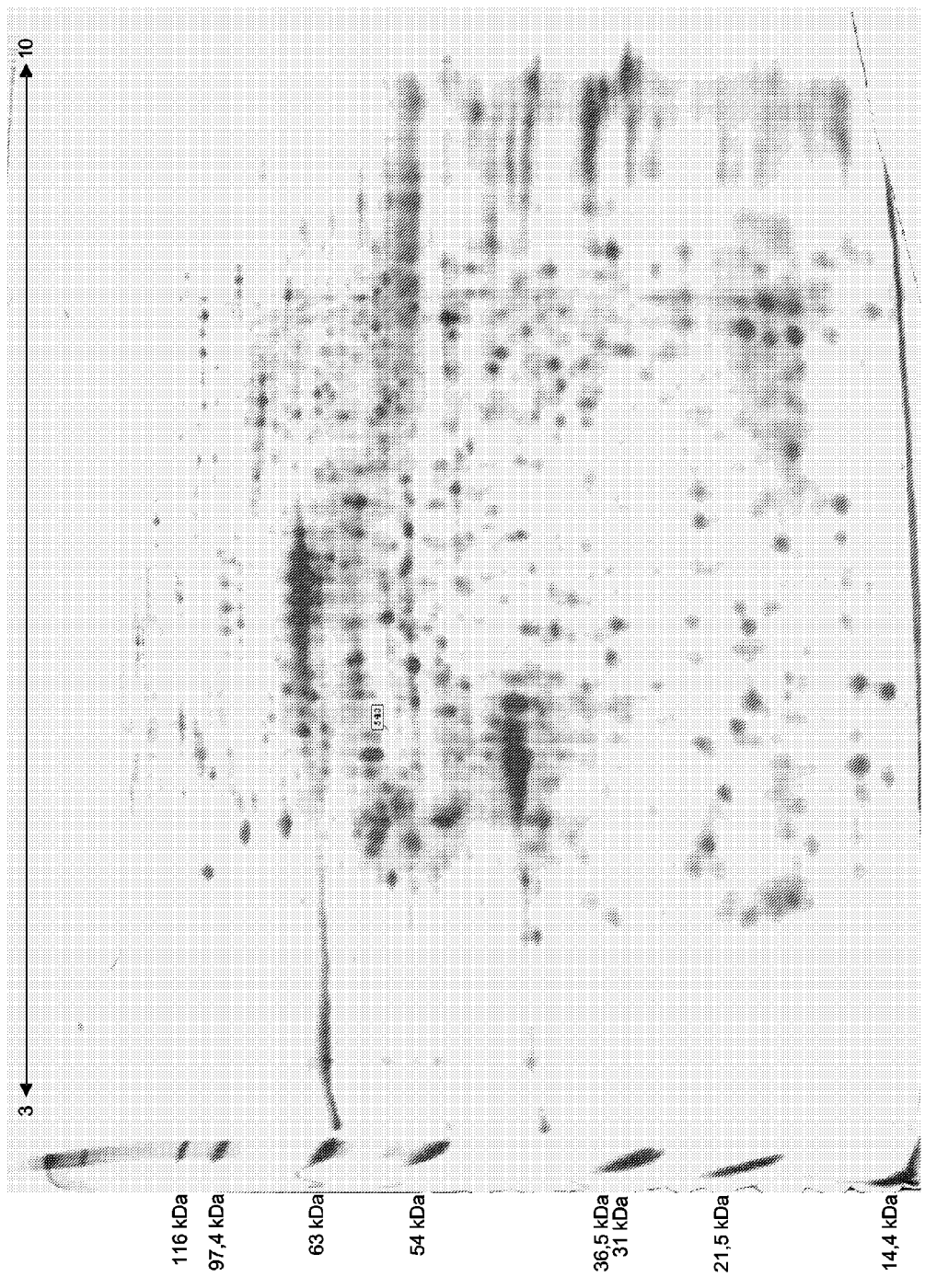
FIGURE 6: 2-D profile of proteins extracted from normal tissue. The pattern shown corresponds to a 2-D PAGE image of silver-stained gel. Spot number indicated protein spots predominant in normal tissue.

| Gels 2 | Control Group | Control Group | Control Group | Control Group | Test Group | Test Group | Test Group | Test Group | counts: 163 counts: 204 | counts: 14 | p(<=0.05)= 126 p(<=0.005)= 13 |
|---|---|---|---|---|---|---|---|---|---|---|---|
| Ref Spot | Spotted in # Gels in Control Group | MEAN | StdDEV | % cov | ed in # Gels in Test Group | MEAN | StdDEV | % cov | REG | TTEST .005 | P.Value |
| 163 | 11 | 0.0420 | 0.0352 | 86 | 12 | 0.1295 | 0.0685 | 53 | 3.08 | SIG | 0.002 |
| 182 | 14 | 0.2310 | 0.1779 | 77 | 13 | 0.5258 | 0.2279 | 43 | 2.28 | SIG | 0.002 |
| 233 | 14 | 0.2069 | 0.1613 | 73 | 13 | 0.4458 | 0.2161 | 48 | 2.15 | SIG | 0.003 |
| 247 | 14 | 0.2740 | 0.1421 | 52 | 13 | 0.5771 | 0.2009 | 35 | 2.11 | SIG | 0.000 |
| 256 | 12 | 0.0759 | 0.0737 | 97 | 12 | 0.1906 | 0.0901 | 47 | 2.5 | SIG | 0.004 |

FIGURE 7 : Number of spots randomly selected by the analysis of faked groups. "SIG" means that the calculated T-Test value is below the limit (0.005).

```
SeqA            MGQFYEAESCLVEAGRLPAGQRRFAHFPGLASELLLTGLPLELIDGSTLS
URG4  PLGVEHFLRE MGQFYEAESCLVEAGRLPAGQRRFAHFPGLASELLLTGLPLELIDGSTLS

SeqA  MPVRWVTGLLKELHVRLERRSRLVVLSTVGVPGTGKSTLLNTMFGLRFATGKSCGPRGAF
URG4  MPVRWVTGLLKELHVRLERRSRLVVLSTVGVPGTGKSTLLNTMFGLRFATGKSCGPRGAF

SeqA  MQLITVAEGFSQDLGCDHILVIDSGGLIGGALTSAGDRFELEASLATLLMGLSNVTVISL
URG4  MQLITVAEGFSQDLGCDHILVIDSGGLIGGALTSAGDRFELEASLATLLMGLSNVTVISL

SeqA  AETKDIPAAILHAFLRLEKTGHMPNYQFVYQNLHDVSVPGPRPRDKRQLLDPPGDLSRAA
URG4  AETKDIPAAILHAFLRLEKTGHMPNYQFVYQNLHDVSVPGPRPRDKRQLLDPPGDLSRAA

SeqA  AQMEKQGDGFRALAGLAFCDPEKQHIWHIPGLWHGAPPMAAVSLAYSEAIFELKRCLLEN
URG4  AQMEKQGDGFRALAGLAFCDPEKQHIWHIPGLWHGAPPMAAVSLAYSEAIFELKRCLLEN

SeqA  IRNGLSNQNKNIQQLIELVRRL
URG4  IRNGLSNQNKNIQQLIELVRRL
```

FIGURE 8: BLAST alignment of the hypothetical protein (SeqA) with the URG4 protein. The amino-acid sequence of the hypothetical protein (1-312) is strictly identical to the c-terminal amino-acid (611-922) of the URG4 protein.

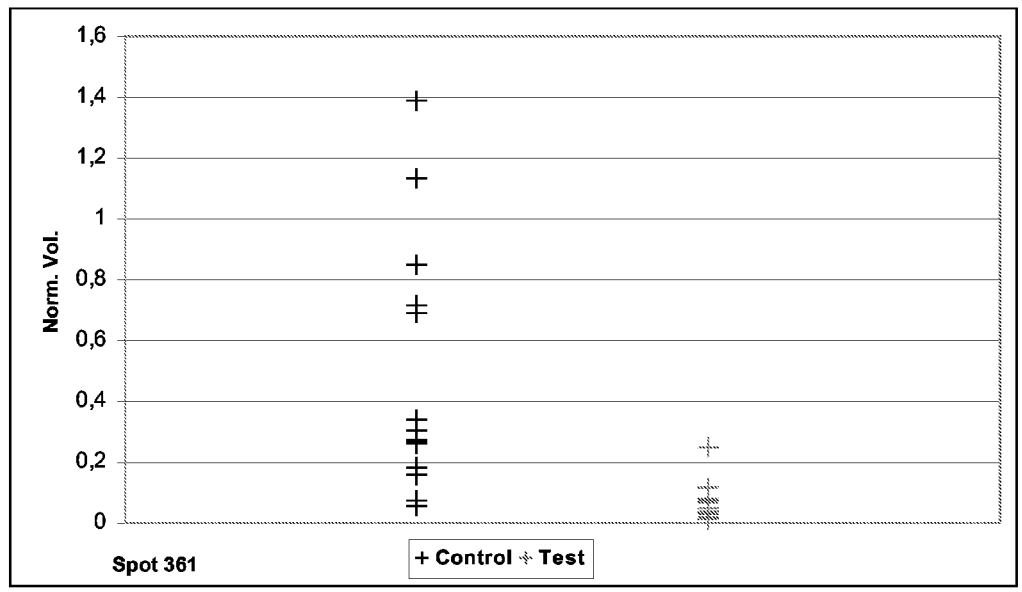
FIGURE 9: Normalized volumes from spot 361 identified as Serotransferrin.
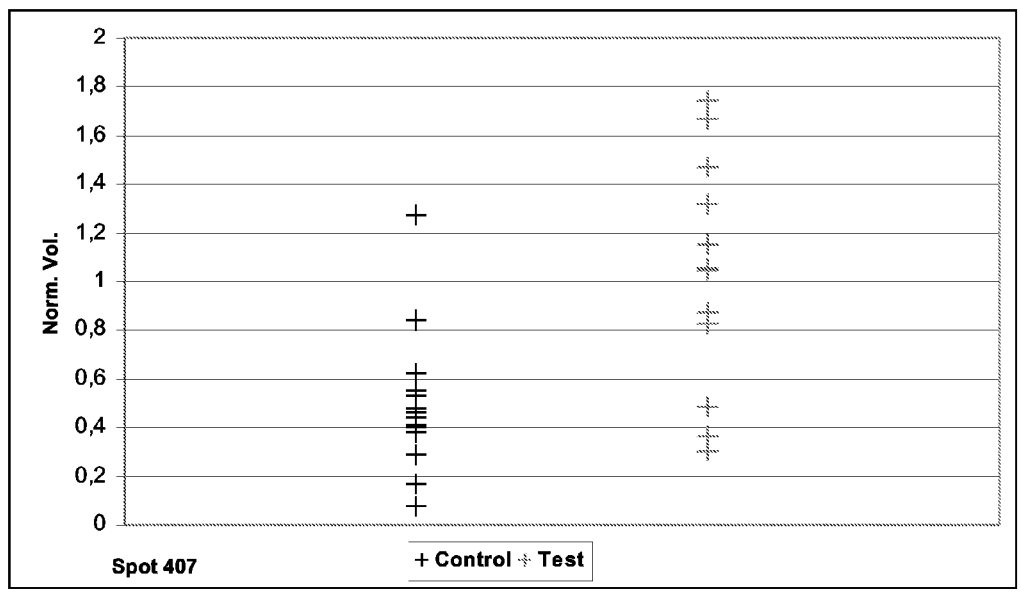
FIGURE 10: Normalized volumes from spot 407 identified as Transforming growth factor-beta induced protein IG-H3.

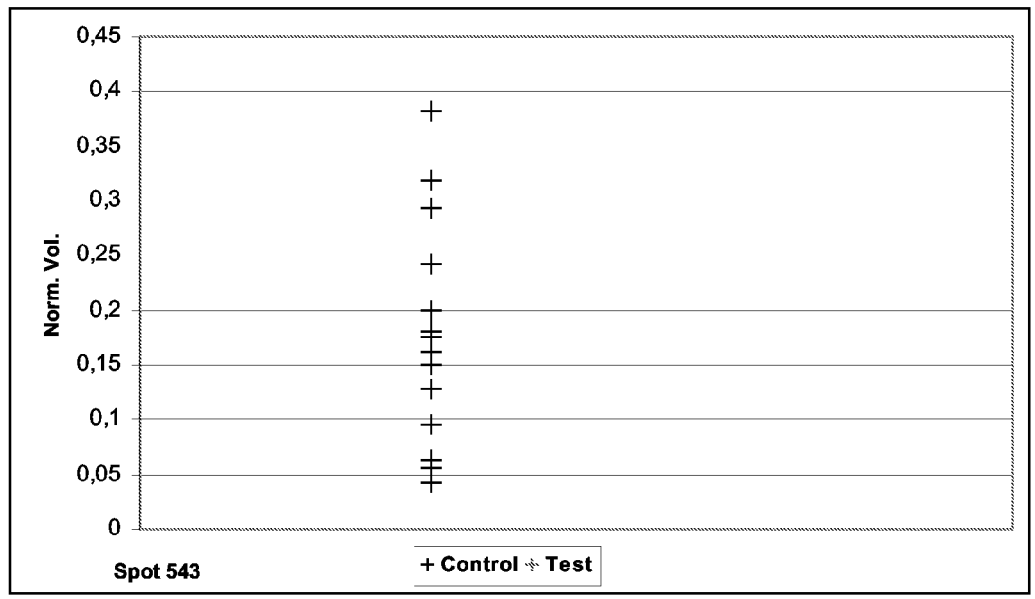
FIGURE 11: Normalized volumes from spot 543 identified as Peripherin.
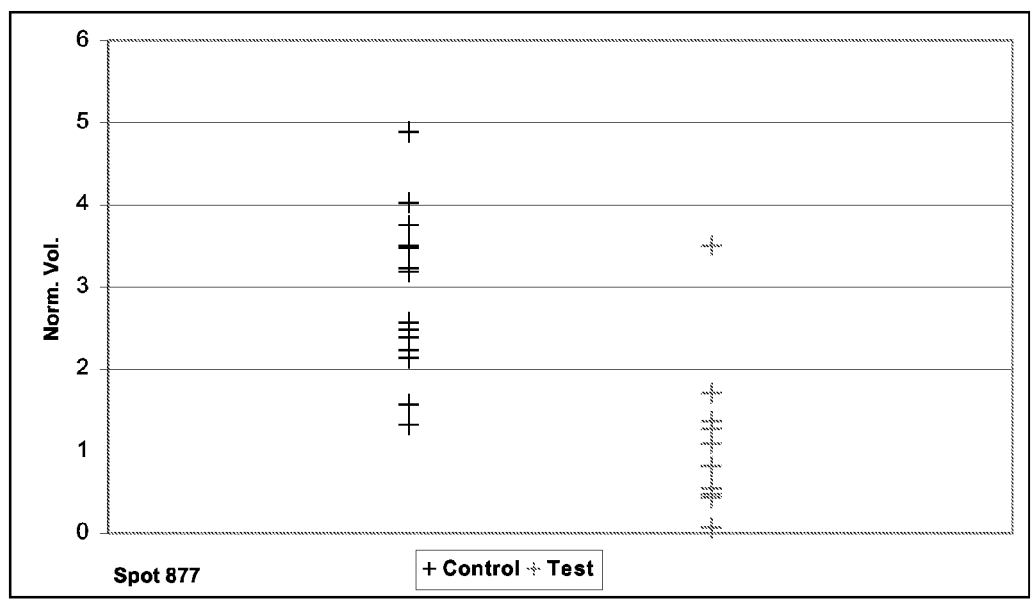
FIGURE 12: Normalized volumes from spot 877 identified as a mixture of two proteins Serum albumin and 26S proteasome subunit p40.5 [Fragment].

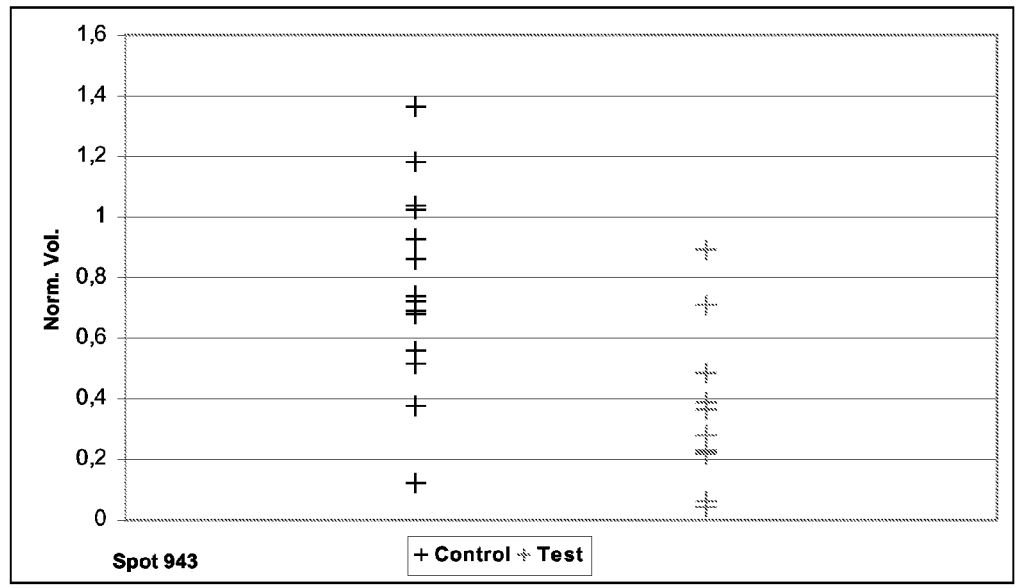
FIGURE 13: Normalized volumes from spot 943 identified as a mixture of two proteins Aldo-keto reductase family 1 member B10 and Fructosamine-3-kinase.
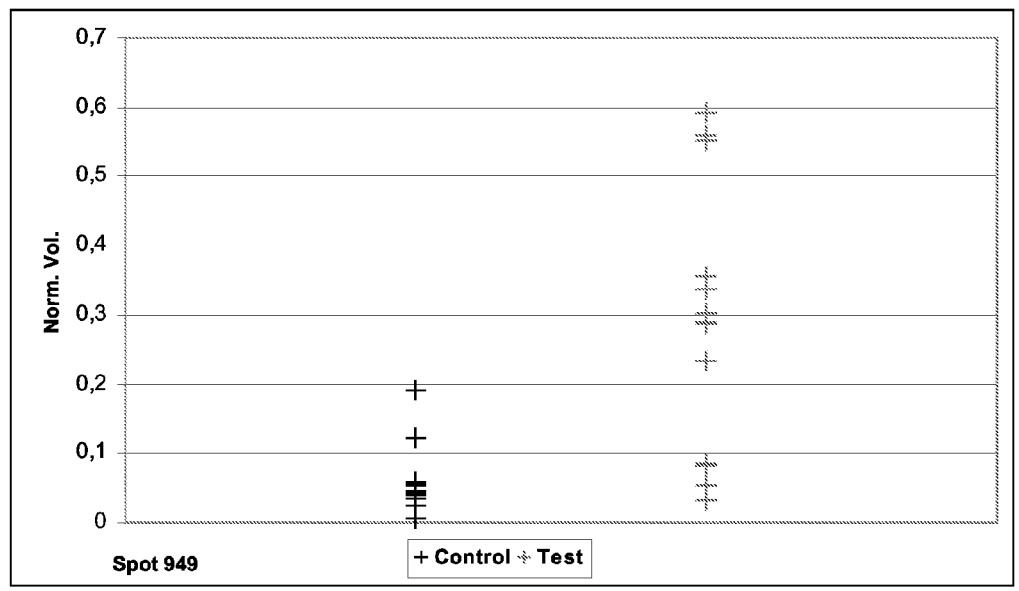
FIGURE 14: Normalized volumes from spot 949 identified as Suppressor of G2 allele of SKP1 homolog.

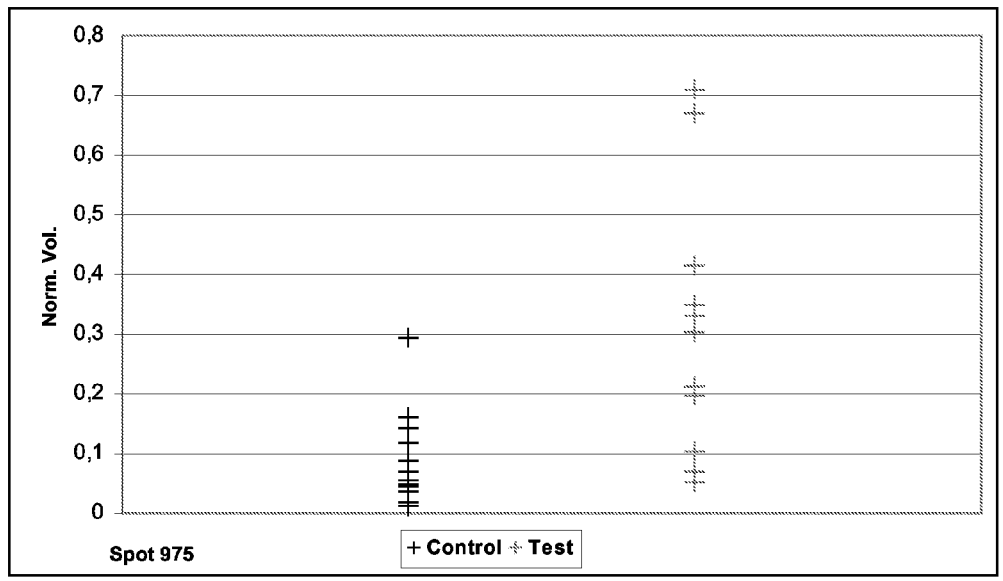
FIGURE 15: Normalized volumes from spot 975 identified as Hypothetical protein.
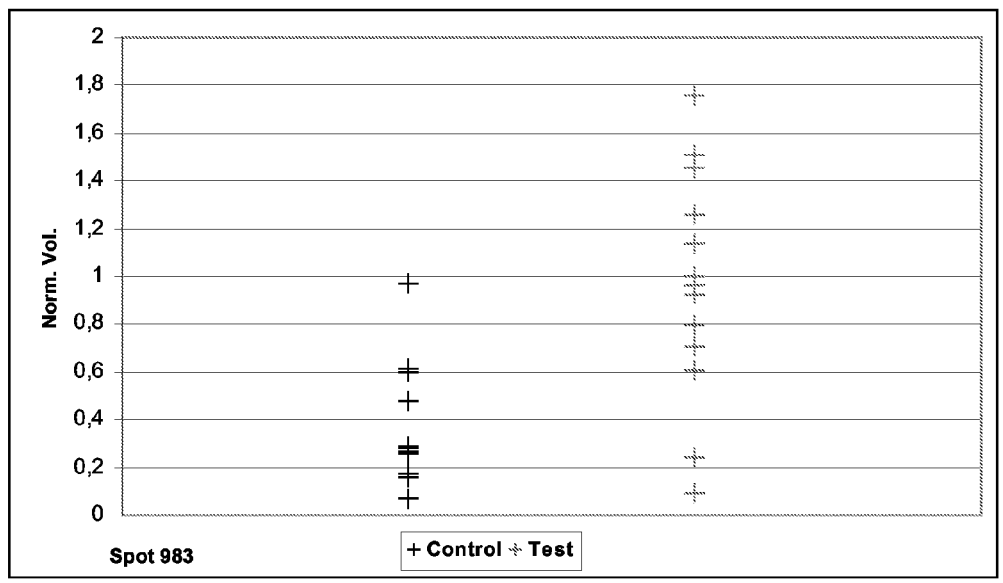
FIGURE 16: Normalized volumes from spot 983 identified as Calponin-2.

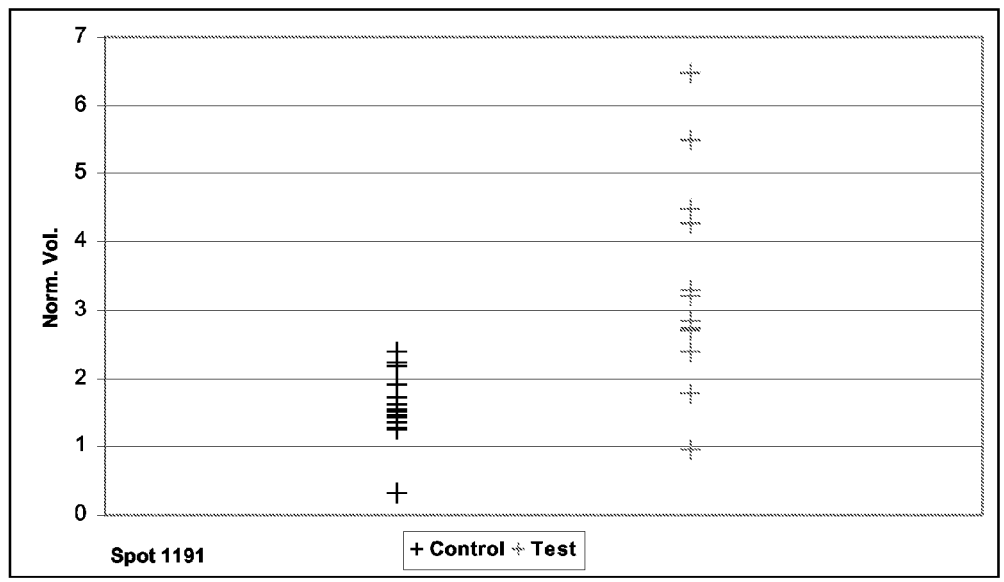
FIGURE 17: Normalized volumes from spot 1191 identified as Heat shock HP-90-beta.
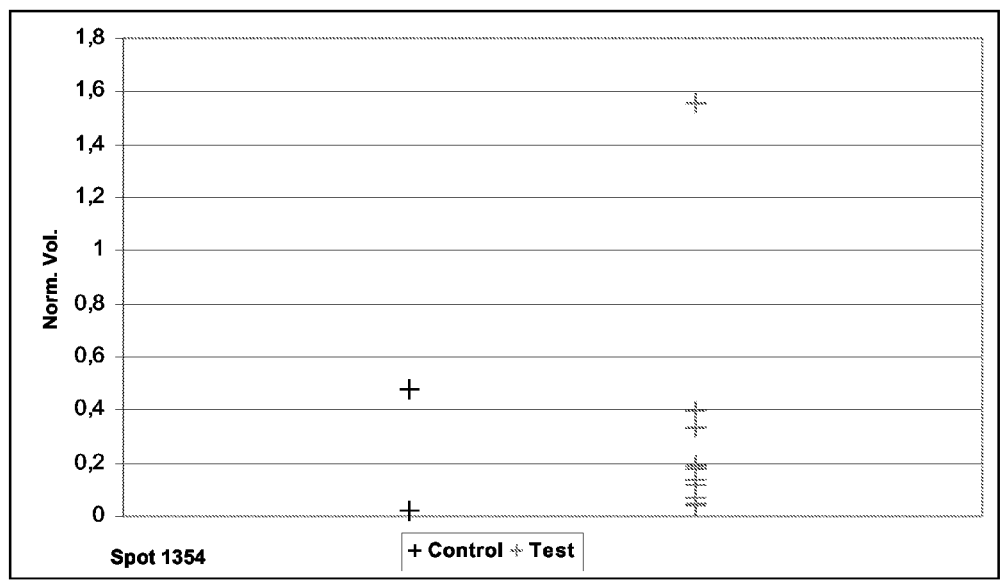
FIGURE 18: Normalized volumes from spot 1354 identified as Phosphoglycerate mutase 1.

| Spot no.[a] | Protein name | Acc. No.[b] | Norm. Vol Control | CV (%) | Norm. Vol Disease | CV (%) | Expression ratio[c] | Mann-Whitney Test | Detection ratio[e] | Theoretical Mr | pI | Cover-age (%) | Number of pept. matched |
|---|---|---|---|---|---|---|---|---|---|---|---|---|---|
| 707 | Alpha-2-macroglobulin | P01023 | 3.286421053 | 33 | 2.18720 | 19 | 0.666 | 0.0008 | 19/15 | 163279 | 6.00 | 17% | 21 |
| 710 | Alpha-2-macroglobulin | P01023 | 2.356052632 | 39 | 1.41553 | 20 | 0.601 | 0.0014 | 19/15 | 163279 | 6.00 | 12% | 18 |
| 711 | Alpha-2-macroglobulin | P01023 | 1.590842105 | 54 | 0.80247 | 33 | 0.504 | 0.0027 | 19/15 | 163279 | 6.00 | 12% | 15 |
| 1040 | SERPIN C1 protein | P01008 | 3.105263158 | 31 | 1.78140 | 53 | 0.574 | 0.0004 | 19/15 | 52692 | 6.12 | 22% | 8 |
| 1149 | Apolipoprotein A-IV | P06727 | 4.928157895 | 38 | 2.60467 | 42 | 0.529 | 0.0000 | 19/15 | 45399 | 5.28 | 61% | 25 |
| 748 | SERPIN C1 protein | P01008 | 0.250947368 | 67 | 0.56913 | 62 | 2.268 | 0.0035 | 19/15 | 52692 | 6.12 | 12% | 5 |
| 2094 | Haptoglobin precursor | P00738 | 2.702210526 | 96 | 7.33780 | 78 | 2.715 | 0.0027 | 19/15 | 46723 | 6.28 | 23% | 9 | a) Spot numbers correspond to spot numbers in Reference gel from Progenesis
b) Accession Number from Swiss-Prot Database
c) Mean normalised spot volume in the disease sample divided by that one in control sample
d) Significance (p) value for the difference in normalised spot volumes (expression ration) compared by Mann-Whitney t-test
e) Number of gel from the control group within the spot was detected / Number of gels from the disease group within the equivalent spot was detected
CV means coefficient of variation FIGURE 19: List of regulated protein spots identified in plasma samples

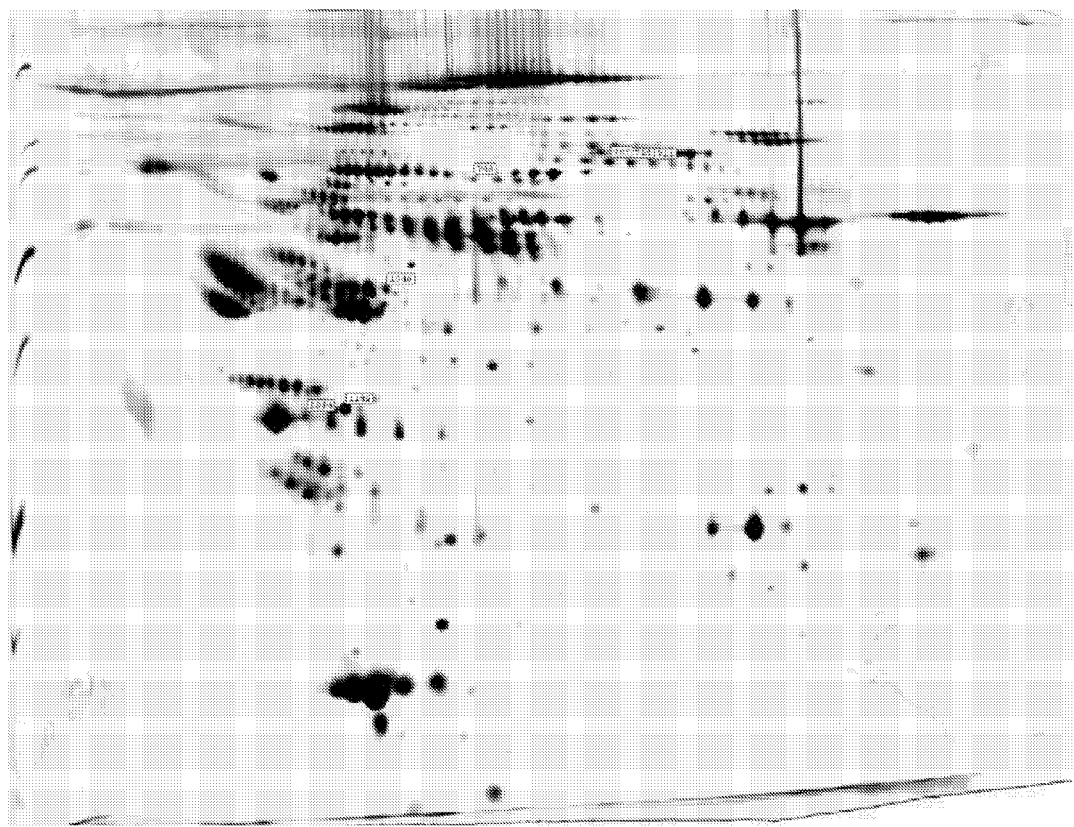
FIGURE 20: 2-DE map of depleted plasma proteome.

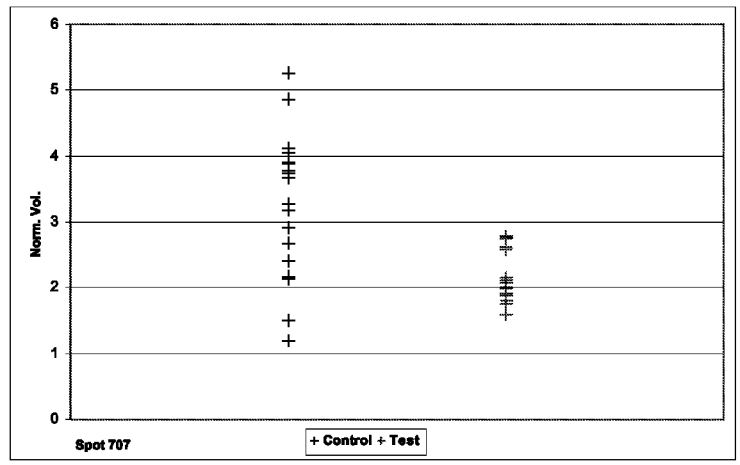
FIGURE 21: Scattergram of spot 707 identified as alpha-2-macroglobulin.
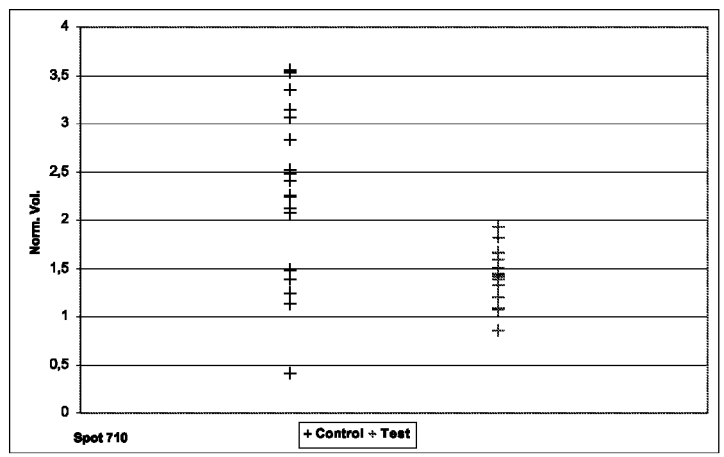
FIGURE 22: Scattergram of spot 710 identified as alpha-2-macroglobulin.

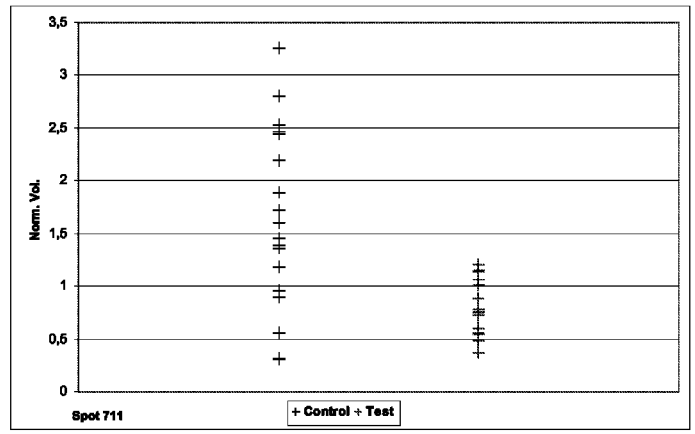
FIGURE 23: Scattergram of spot 711 identified as alpha-2-macroglobulin.
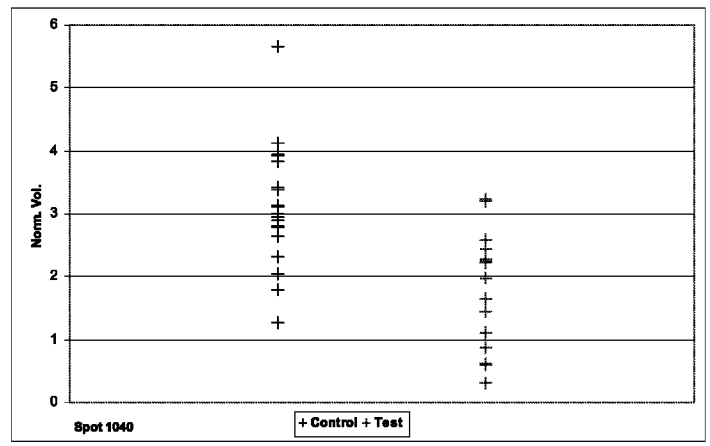
FIGURE 24: Scattergram of spot 1040 identified as SERPIN C1 protein (Antithrombin 3).

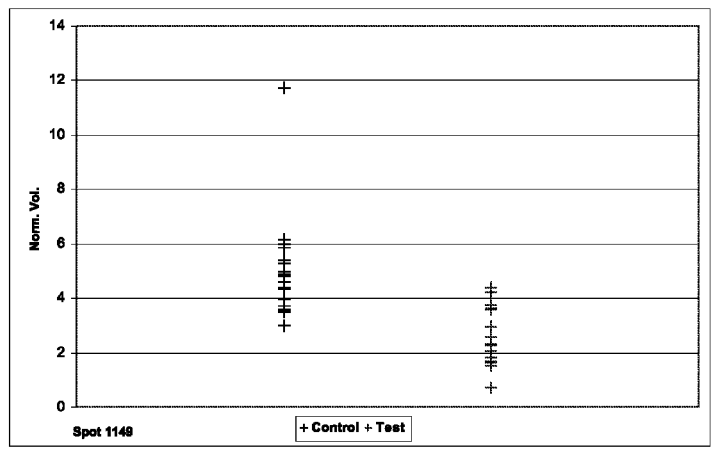
FIGURE 25: Scattergram of spot 1149 identified as Apolipoprotein A-IV.
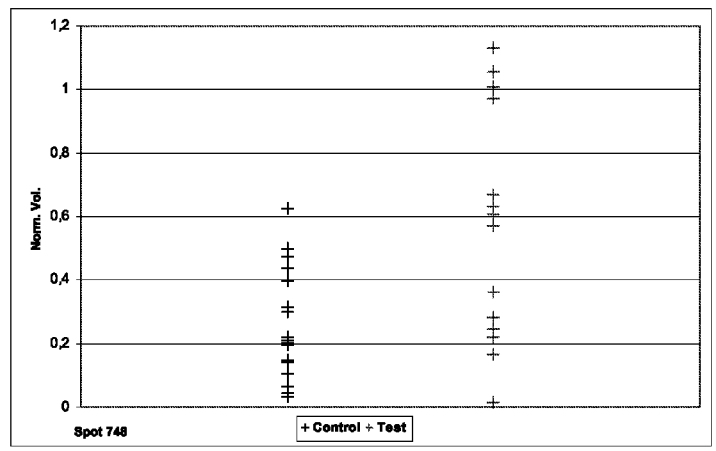
FIGURE 26: Scattergram of spot 748 identified as SERPIN C1 protein (Antithrombin 3).

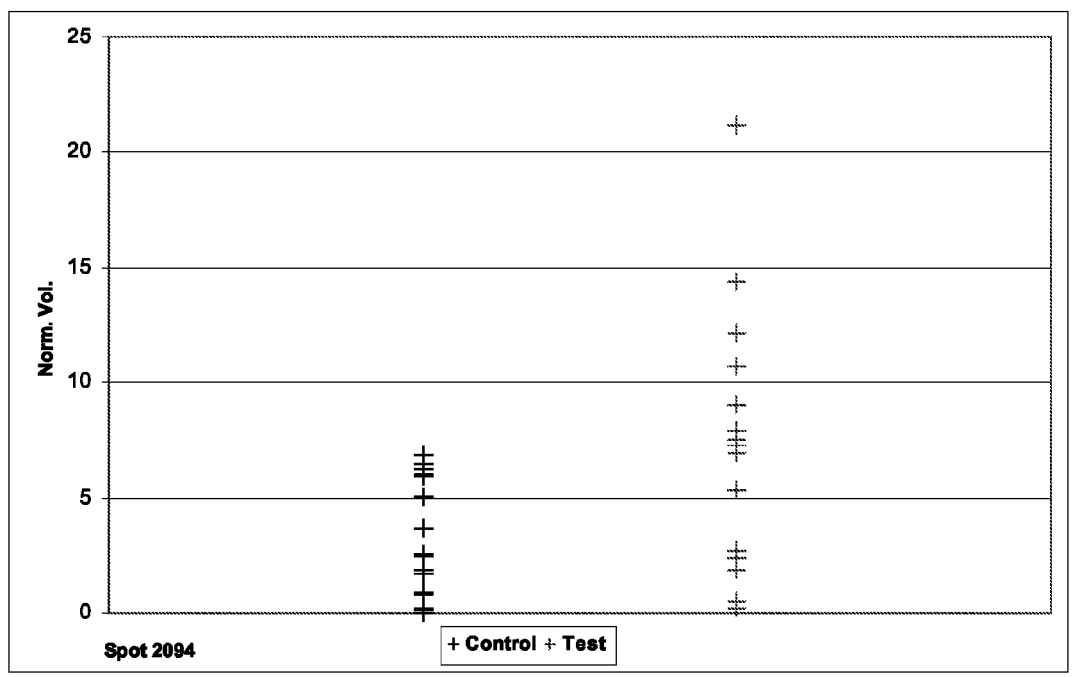
FIGURE 27: Scattergram of spot 2094 identified as Haptoglobin precursor.

DIAGNOSIS AND PROGNOSIS OF COLORECTAL CANCER

CROSS-REFERENCE TO RELATED APPLICATION

This application is a National Stage entry of International Application No. PCT/GB2006/050460, filed Dec. 15, 2006. The disclosure of the prior application is hereby incorporated herein in its entirety by reference.

SEQUENCE LISTING

The instant application contains a Sequence Listing which has been submitted electronically in ASCII format and is hereby incorporated by reference in its entirety. Said ASCII copy, created on Dec. 18, 2013, is named 108140-00092_SL.txt and is 6,107 bytes in size.

BACKGROUND OF THE INVENTION

1. Field of the Invention

This invention relates to the diagnosis and prognosis of colorectal cancer.

2. Description of the Related Art

Colorectal cancer (CRC) is the third most frequent cancer in the world. Serum tumour markers such as carcinoembryonic antigen (CEA) (Gold and Freedman, 1965), cytokeratins (Moll et al. 1982), CA19-9, CA 242 (Nilsson et al. 1992), CA 72-4 (Fernandez-Fernandez et al. 1995), VEGF (Broll et al. 2001), p53 (Shiota et al. 2000; Hammel et al. 2000), HNP 1-3 (Albrethsen et al. 2005), RCAS1 (Yamagushi et al. 2005), Apolipoprotein A-I, Apolipoprotein C-I (Engwegen et al. 2006), Complement C3a des-arg, alpha-1-antitrypsin, transferring (Ward et al. 2006) and PSME3 (Roessler et al. 2006) have been identified. However, there is a need to find new biomarkers for CRC in tumour tissue samples and body fluid (e.g. plasma) samples.

SUMMARY OF THE INVENTION

The present invention provides a method of diagnosis of colorectal cancer in a diagnostic sample of a valid body tissue taken from a human subject, which comprises detecting an increased concentration of a protein in the diagnostic sample, compared with a control, normal human sample, the protein being:
transforming growth factor-beta induced protein IG-H3 (SwissProt Acc. No. Q15582);
suppressor of G2 allele of SKP1 homolog (isoform 2) (SwissProt Acc. No. Q9Y2Z0-2);
hypothetical protein (part of URG4) (SwissProt Acc. No. Q9NWR7);
calponin-2 (SwissProt Acc. No. Q99439);
heat shock protein HSP90-beta (SwissProt Acc. No. P08238);
phosphoglycerate mutase 1 (SwissProt Acc. No. P18669);
serpin C1 protein (SwissProt Acc. No. P01008); or
haptoglobin precursor (SwissProt Acc. No. P00738);
or a decreased concentration of a protein in the diagnostic sample, compared with a control, normal human sample, the protein being serotransferrin (SwissProt Acc. No. P02787);
26S proteasome subunit p40.5 (Swiss Prot Acc. No. Q9UNM7);
aldo-keto reductase family 1 member B10 (SwissProt Acc. No. O60218);
fructosamine-3-kinase (SwissProt Acc. No. Q9H479);
peripherin (SwissProt Acc. No. P41219);
alpha-2-macroglobulin (SwissProt Acc. No. P01023);
serpin C1 protein (SwissProt Acc. No. P01008); or
apolipoprotein A IV (SwissProt Acc. No. P06727).

The above proteins are referred to herein as "marker proteins" or "biomarkers".

The same proteins can be used for prognosis by detecting changes in their concentration in the course of treatment for colorectal cancer. Thus, the invention also provides a method of monitoring the effect of a treatment for colorectal cancer in a subject, which comprises detecting a change in concentration of at least one protein in a sample of a valid body tissue taken from said subject at a stage in said treatment, compared with the concentration of said protein in a sample of a valid body tissue taken from said subject prior to said treatment or at an earlier stage in said treatment, the protein being at least one of those specified above.

Although there is a high degree of confidence in the identification of the marker proteins specified above, the invention can be defined alternatively in terms of the proteins within the differentially expressed spots on a two dimensional electrophoretic gel, namely those identified in FIGS. 3 to 6 herein, without regard to the names and database identifications given above.

DEFINITIONS

The term "protein" (also referred to as "polypeptide") is not restricted to the sequences corresponding to the accession numbers given above, and includes variants, mutants and isoforms thereof. A variant is defined as a naturally occurring variation in the sequence of a polypeptide which has a high degree of homology with the given sequence, and which has substantially the same functional and immunological properties. A mutant is defined as an artificially created variant. A high degree of homology is defined as at least 90%, preferably at least 95% and most preferably at least 99% homology. Variants may occur within a single species or between different species. An isoform of a polypeptide has the same function as the polypeptide but is encoded by a different gene and may have small differences in its sequence. The above proteins are of human origin, but the invention encompasses use of the corresponding polypeptides from other mammalian species.

The term "differentially expressed" means that the stained protein-bearing spots are present at a higher or lower optical density in the gel from the sample taken for diagnosis (the "diagnostic sample") than the gel from a control or other comparative sample. It follows that the proteins are present in the diagnostic sample at a higher or lower concentration than in the control or other comparative sample.

The term "control" refers to a normal human subject, i.e. one not suffering from CRC, or to healthy tissue of the same human subject as the diagnostic sample.

The terminology "increased/decreased concentration . . . compared with a control sample" does not imply that a step of comparing is actually undertaken, since in many cases it will be obvious to the skilled practitioner that the concentration is abnormally high or low. Further, when the stages of CRC are being monitored progressively, or when a course of treatment is being monitored, the comparison made can be with the concentration previously seen in the same subject at an earlier stage of progression of the disease, or at an earlier stage of treatment or before treatment has commenced.

The term "binding partner" includes a substance that recognises or has affinity for the marker protein. It may or may not itself be labelled.

The term "antibody" includes polyclonal antiserum, monoclonal antibodies, fragments of antibodies such as single chain and Fab fragments, and genetically engineered antibodies. The antibodies may be chimeric or of a single species.

The term "marker protein" or "biomarker" includes all biologically relevant forms of the protein identified, including post-translational modification. For example, the marker protein can be present in the body tissue in a glycosylated, phosphorylated, multimeric or precursor form.

The term "diagnosis", as used herein, includes determining whether CRC is present or absent and also includes determining the stage to which it has progressed (or regressed in the course of treatment). The diagnosis can serve as the basis of a prognosis as to the future outcome for the patient.

The term "valid body tissue" means any tissue in which it may reasonably be expected that a marker protein would accumulate in relation to CRC. It may be a colorectal sample, or it may be a body fluid, e.g. blood or a blood derivative such as plasma or serum.

The term "antibody array" or "antibody microarray" means an array of unique addressable elements on a continuous solid surface whereby at each unique addressable element an antibody with defined specificity for an antigen is immobilised in a manner allowing its subsequent capture of the target antigen and subsequent detection of the extent of such binding. Each unique addressable element is spaced from all other unique addressable elements on the solid surface so that the binding and detection of specific antigens does not interfere with any adjacent such unique addressable element.

The term "bead suspension array" means an aqueous suspension of one or more identifiably distinct particles whereby each particle contains coding features relating to its size and colour or fluorescent signature and to which all of the beads of a particular combination of such coding features is coated with an antibody with a defined specificity for an antigen in a manner allowing its subsequent capture of the target antigen and subsequent detection of the extent of such binding.

BRIEF DESCRIPTION OF THE FIGURES

FIG. 1 is a table of results from Example 1 below, displaying for each gel the number of spots detected, the sum of volume of all spots and the scaling factor.

FIG. 2 is a table of results from Example 1 below, showing the proteins detected in each spot.

FIG. 3 is a photograph of a two-dimensional gel of proteins extracted from tumour tissue by the method described in Example 1. The pattern shown corresponds to a 2-D PAGE image of a silver-stained gel. Molecular weight markers in kiloDaltons (kDa) are shown on the ordinate, and the isoelectric point (pI) is shown on the abscissa, increasing from left to right. The spot numbers indicate protein spots which are up-regulated in tumour tissue.

FIG. 4 is a photograph of a similar gel, in which the spot numbers indicate proteins spots which predominate in tumour tissue.

FIG. 5 is a photograph of a similar gel, in which the spot numbers indicate protein spots which are down-regulated in tumour tissue.

FIG. 6 is a photograph of a corresponding gel of proteins extracted from normal tissue, in which the spot numbers indicate protein spots which are predominant in normal tissue.

FIG. 7 is a table showing the number of spots randomly selected by the analysis of faked groups, as described below in Example 1.

FIG. 8 shows the BLAST alignment of the hypothetical protein (SeqA) (SEQ ID NO: 1) with the URG4 protein (SEQ ID NO: 2). The amino acid sequence of the hypothetical protein (1-312) is strictly identical to the C-terminal amino acid sequence (611-922) of the URG4 protein.

FIG. 9 is a scattergram showing the normalised volumes from spot 361 identified as serotransferrin. "Control" means normalised volume intensities from spots detected in control sample gels and "Test" means normalised volume intensities from spots detected in tumour sample gels.

FIG. 10 is a corresponding scattergram showing the normalised volumes from spot 407 identified as transforming growth factor-beta induced protein IG-H3.

FIG. 11 is a corresponding scattergram showing the normalised volumes from spot 543 identified as peripherin.

FIG. 12 is a corresponding scattergram showing the normalised volumes from spot 877 identified as a mixture of two proteins: serum albumin and 26S proteasome subunit p40.5.

FIG. 13 is a corresponding scattergram showing the normalised volumes from spot 943 identified as a mixture of two proteins: aldo-keto reductase family 1 member B10 and fructosamine-3-kinase.

FIG. 14 is a corresponding scattergram showing the normalised volumes from spot 949 identified as suppressor of G2 allele of SKP1 homolog (isoform 2).

FIG. 15 is a corresponding scattergram showing the normalised volumes from spot 975 identified as hypothetical protein (part of URG4).

FIG. 16 is a corresponding scattergram showing the normalised volumes from spot 983 identified as calponin-2.

FIG. 17 is a corresponding scattergram showing the normalised volumes from spot 1191 identified as heat shock protein HSP90-beta.

FIG. 18 is a corresponding scattergram showing the normalised volumes from spot 1354 identified as phosphoglycerate mutase 1.

FIG. 19 is a table of results from Example 2 below, showing the proteins detected in each spot.

FIG. 20 is a photograph of a two-dimensional gel of proteins extracted from plasma samples by the method described in Example 2.

FIG. 21 is a scattergram of spot 707 identified as alpha-2-macroglobulin, as described in Example 2.

FIG. 22 is a corresponding scattergram of spot 710 identified as alpha-2-macroglobulin.

FIG. 23 is a corresponding scattergram of spot 711 identified as alpha-2-macroglobulin.

FIG. 24 is a corresponding scattergram of spot 1040 identified as SERPIN C1 protein (Antithrombin 3).

FIG. 25 is a corresponding scattergram of spot 1149 identified as Apolipoprotein A-IV.

FIG. 26 is a corresponding scattergram of spot 748 identified as SERPIN C1 protein (Antithrombin 3).

FIG. 27 is a corresponding scattergram of spot 2094 identified as Haptoglobin precursor.

In FIGS. 9 to 18 and 21 to 27 the results for the 'Control' are shown to the left of the results for the 'Test'.

DESCRIPTION OF PREFERRED EMBODIMENTS

A preferred method of diagnosis comprises performing a binding assay for the marker protein. Any reasonably specific binding partner can be used. Preferably the binding partner is labelled. Preferably the assay is an immunoassay, especially between the marker and an antibody that recognises the protein, especially a labelled antibody. It can be an antibody raised against part or all of it, most preferably a monoclonal antibody or a polyclonal anti-human antiserum of high specificity for the marker protein.

Thus, the marker proteins described above are useful for the purpose of raising antibodies thereto which can be used to detect the increased or decreased concentration of the marker proteins present in a diagnostic sample. Such antibodies can be raised by any of the methods well known in the immunodiagnostics field.

The antibodies may be anti- to any biologically relevant state of the protein. Thus, for example, they can be raised against the unglycosylated form of a protein which exists in the body in a glycosylated form, against a more mature form of a precursor protein, e.g. minus its signal sequence, or against a peptide carrying a relevant epitope of the marker protein.

The sample can be taken from any valid body tissue, especially body fluid, of a (human) subject, but preferably blood, plasma or serum. Other usable body fluids include cerebrospinal fluid (CSF), urine and tears.

The preferred immunoassay is carried out by measuring the extent of the protein/antibody interaction. Any known method of immunoassay may be used. A sandwich assay is preferred. In this method, a first antibody to the marker protein is bound to the solid phase such as a well of a plastics microtitre plate, and incubated with the sample and with a labelled second antibody specific to the protein to be assayed. Alternatively, an antibody capture assay can be used. Here, the test sample is allowed to bind to a solid phase, and the anti-marker protein antibody is then added and allowed to bind. After washing away unbound material, the amount of antibody bound to the solid phase is determined using a labelled second antibody, anti- to the first.

In another embodiment, a competition assay is performed between the sample and a labelled marker protein or a peptide derived therefrom, these two antigens being in competition for a limited amount of anti-marker protein antibody bound to a solid support. The labelled marker protein or peptide thereof can be pre-incubated with the antibody on the solid phase, whereby the marker protein in the sample displaces part of the marker protein or peptide thereof bound to the antibody.

In yet another embodiment, the two antigens are allowed to compete in a single co-incubation with the antibody. After removal of unbound antigen from the support by washing, the amount of label attached to the support is determined and the amount of protein in the sample is measured by reference to standard titration curves established previously.

The label is preferably an enzyme. The substrate for the enzyme may be, for example, colour-forming, fluorescent or chemiluminescent.

The binding partner in the binding assay is preferably a labelled specific binding partner, but not necessarily an antibody. The binding partner will usually be labelled itself, but alternatively it may be detected by a secondary reaction in which a signal is generated, e.g. from another labelled substance.

It is highly preferable to use an amplified form of assay, whereby an enhanced "signal" is produced from a relatively low level of protein to be detected. One particular form of amplified immunoassay is enhanced chemiluminescent assay. Conveniently, the antibody is labelled with horseradish peroxidase, which participates in a chemiluminescent reaction with luminol, a peroxide substrate and a compound which enhances the intensity and duration of the emitted light, typically 4-iodophenol or 4-hydroxycinnamic acid.

Another preferred form of amplified immunoassay is immuno-PCR. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 23: 522-529 (1995). The signal is read out as before.

Alternatively, the diagnostic sample can be subjected to two dimensional gel electrophoresis to yield a stained gel and the increased or decreased concentration of the protein detected by an increased or decreased intensity of a protein-containing spot on the stained gel, compared with a corresponding control or comparative gel. The relevant spots and differential expression are those listed in FIG. 2 as described below. The invention includes such a method, independently of the marker protein identification given above and in FIG. 2.

In another embodiment, the diagnostic sample is a tissue section which is fixed, e.g. by freezing or embedding in paraffin, and then subjected to immunohistochemistry.

In a further embodiment, the diagnostic sample is subjected to in situ hybridisation using a DNA probe for a messenger RNA of at least one of the proteins specified above.

In a still further embodiment an increased concentration of one or more of the following marker proteins which are over-expressed in CRC:

transforming growth factor-beta induced protein IG-H3 (SwissProt Acc. No. Q15582);
suppressor of G2 allele of SKP1 homolog (isoform 2) (SwissProt Acc. No. Q9Y2Z0-2);
hypothetical protein (part of URG4) (SwissProt Acc. No. Q9NWR7);
calponin-2 (SwissProt Acc. No. Q99439);
heat shock protein HSP90-beta (SwissProt Acc. No. P08238);
phosphoglycerate mutase 1 (SwissProt Acc. No. P18669);
serpin C1 protein (SwissProt Acc. No. P01008); or
haptoglobin precursor (SwissProt Acc. No. P00738);
is detected by detecting an elevated level of autoantibody thereto, compared with the level of autoantibody in the control sample. The level of autoantibody can be detected by western blot (from 1D or 2D electrophoresis) against own tumour, autologous tumour or CRC cell lines, by enzyme-linked immunosorbent assay (ELISA), protein microarray or bead suspension array using purified proteins.

By way of example, detection of autoantibodies to proteins differentially increased in colorectal cancer patients can be carried out as follows. Recombinant proteins are expressed in baculovirus infected insect cells and used to coat the surface of microtitre plates. Serum/plasma drawn from patients suspected of having colorectal cancer is added to duplicate wells of each microtitre plate and incubated at 37° C. for 1 hour. Plates are aspirated and washed prior to the addition of a horse-radish peroxidase (HRP) labelled anti-human IgG antiserum and incubated for 1 hour at 37° C. Finally, binding of the antihuman antiserum is revealed by aspirating the plates, washing, and then adding tetra-methylbenzidine (TMB) which in the presence of HRP produces a coloured product the intensity of which is measured by reading the plates at 450 nm. An identical set of plates is tested with the exception that the second antibody is a HRP labelled anti-human IgM antiserum. The levels of IgG and/or IgM autoantibodies to each of the CRC marker proteins is elevated when compared to the levels found in the serum of healthy individuals without colorectal cancer.

The diagnosis does not necessarily require a step of comparison of the concentration of the protein (or autoantibody) with a control, but it can be carried out with reference either to a control or a comparative sample. The invention can be used to determine the stage of progression of CRC, if desired with reference to results obtained earlier from the same patient or by reference to standard values that are considered typical of the stage of the disease. In this way, the invention can be used to determine whether, for example after treatment of the patient with a drug or candidate drug, the disease has progressed or not. The result can lead to a prognosis of the outcome of the disease.

The invention further includes the use for a diagnostic (and thus possibly prognostic) or therapeutic purpose of a partner material which recognises, binds to or has affinity for a marker protein specified above and/or represented by a differentially expressed two dimensional gel electrophoretic spot shown in any of FIGS. 3 to 6. Thus, for example, antibodies to the marker proteins, appropriately humanised where necessary, may be used in treatment. The partner material will usually be an antibody and used in any assay-compatible format, conveniently an immobilised format, e.g. as beads or a chip. Either the partner material will be labelled or it will be capable of interacting with a label.

The invention further includes a kit for use in a method of diagnosis, which comprises a partner material, as described above, in an assay-compatible format, as described above, for interaction with a protein present in the diagnostic sample.

The invention further includes a kit for use in a method of diagnosis, which comprises a differentially expressed protein as described above, in an assay-compatible format, as described above, for interaction with an autoantibody present in the diagnostic sample. The diagnosis can be based on the differential expression of one, two, three or more of the marker proteins, or of one, two, three or more autoantibodies raised against such proteins, or a combination of both. Further, it can be part of a wider diagnosis in which two or more different diseases are diagnosed. CRC can be diagnosed together with at least one other disease, which may or may not be a cancer, in the same sample of body tissue, by a method which includes detecting a change in concentration of another protein in the diagnostic sample, compared with a sample of a control, normal human subject. These other disease(s) can be any which are diagnosable in a body tissue.

Thus, in particular, it is contemplated within the invention to use an antibody chip or array of chips, capable of detecting one or more proteins that interact with that antibody; a protein chip or array of chips, capable of detecting one or more autoantibodies that interact with the proteins differentially expressed in colorectal cancer; a combination of both antibody arrays and protein arrays.

The following Examples illustrate the invention.

Example 1

15 patients were selected. From these patients, 15 colorectal samples corresponding to tumour tissues and 15 samples corresponding to neighbouring normal tissues were taken. Tumour and normal tissue samples were placed in a container on liquid nitrogen and homogenized to a powder-like consistency.

2D Gel Electrophoresis (2DE) and Mass Spectrometry (MS)

Prior to the experimental work, a 2DE separation optimization step was performed to cover a maximum number of proteins displayed with a minimum number of 2D gels. Several IPG (immobilized pH gradient) strip ranges were tested: 4-7, 3-7NL (NL=non-linear), 3-10 and 3-10NL. In our hands, the best range was 3-10Non-Linear. For each sample, a single analytical gel was run (pH 3-10NL, 10% Acrylamide, 100 µg protein load). The gels were silver-stained, scanned and the gel images were analysed with ProGenesis software (v2005).

Due to the fact that 2 tumour tissue samples were degraded, the tumour tissue group was based on 13 analytical gels. The normal tissue group was based on 14 analytical gels, because one gel was removed from the image analysis (spots were smearing/diffuse). The two groups of gels were compared to each other. To select regulated spots, we used the following criteria: spots present within at least 60% of gels, 2 fold down/up regulation and p value<0.005.

For the preparative gels, 4 normal samples were mixed together (Normal Tissue Mix) and 4 tumour samples were mixed together (Tumour Tissue Mix) and 500 µg protein of each mix sample were loaded onto the first IPG (pH 3-10NL, 10% Acrylamide). The gels were Commassie-stained and scanned.

The protein spots of interest were picked from the preparative gels, and treated with Spot Handling Workstation (GE Healthcare). The peptide profiles were generated with MALDI-ToF (matrix-assisted laser desorption ionization mass spectrometry, analysis by time of flight), analysed with Ms-Fit software (Protein Prospector) and searched against IPI (International Protein Index) database.

Results

Image Analysis Strategy and Number of Regulated Protein Spots of Interest

Gel images were analysed with ProGenesis (v2005). Spot detection, matching, background subtraction and normalisation were automatically performed by ProGenesis. The background subtraction method used was the proprietary background subtraction algorithm developed by Nonlinear Dynamics. The algorithm calculated a background level based on a surface model of the entire gel. The normalisation mode used was the "Total Spot Volume" method. In this method, the volume of each spot is divided by the total volume of all of the spots in the gel. Since this method tends to produce extremely small values, the result was multiplied by a factor. For example, if 100 is used as a factor, which is the default value, a Spot Percentage volume will be produced. We decided that multiplication by a factor of 1000 enables larger integers to be used in the data analyses than the default value indicated by ProGenesis. Then the spot data were exported to Excel and a macro was used to calculate Coefficient of Variation (CV in %), Student T-Test, Mann-Whitney test and Regulation factor between tumour versus normal spot volume ratio within the 99.5th confidence level (p<0.005).

FIG. 1 displays for each gel the number of spots detected, the sum of volume of all spots (IOD) and the scaling factor—S.F.—(the sum of the volume of all spots in the Reference Gel divided by the sum of volume of all spots in the gel). In FIG. 1, for each gel, the number of detected spots, the sum of volume (IOD) of all spots and the scaling factor (S.F.) are indicated. Gel n_03-0562_2217 corresponds to the Reference gel. In this table, we can observe that all gels have a scaling factor above the empiric values (0.6<S.F.<1.5). These 27 gels were incorporated into the image analysis.

Based on our experience, we applied these selection criteria—spots have to be found within at least 60% of gels, 2-fold up/down change within the 99.5th confidence level (Student's t-test and/or Mann-Whitney test; p<0.005). With the prerequisite of spot presence within 60% of gels, around 900 spots went into the statistical analysis. 31 spots were found to be differentially expressed between tumour and normal tissues. These spots are listed in FIG. 2. 18 spots are up-regulated or pre-dominant in tumour tissue group and 13 spots are down-regulated or predominant in normal tissue group. The spot locations in the gels are indicated in FIGS. 3-6. Scattergrams of normalized volumes from selected spots are shown in FIGS. 9-18.

The 99.5th confidence level is a very narrow interval that implies high precision and consequently represents a very stringent criterion. Indeed, a p value of 0.005 means that this result would have arisen by chance on less than one occasion in 200 or in other words, from 200 selected spots, one may be expected to be randomly selected. In our case, with the 99.5th confidence level, around 5 spots from 900 could be randomly selected.

All statistical analysis of normalised data should be accompanied by its negatively controlled analysis of the data. One of these negative controls is the analysis of faked groups, i.e. by mixing data columns. For example, if an experiment consists of 6 control gels and experimental gels then the two groups compared should contain 3 control+3 experimental gels each (faked group). This "faked group" comparison will (i) indicate how many spots could be randomly selected and (ii) ensure that robust regulated spots from the real comparisons are selected with a true statistical significance, by ignoring underlying noise of the data set under the analysis. From carrying out this type of test, it will become evident what type of selection criteria will permit real changes to be identified within experimental groups. If, after carrying out the "faked group" comparison, one finds the similar number of changes as the real comparison then the data set is "empty" in terms of group specific changes.

Consequently we made 2 faked groups by mixing half of normal tissue gels with half of tumour tissue gels and compared faked group 1 with faked group 2. The faked groups analysis contains all the gels that were included in the real comparison. For this faked group analysis, we used the same spot selection strategy (within 60% of gels, p<0.005 and 2 fold change). As indicated in the table of FIG. 7, 5 spots have been selected, which corresponds to the theoretical value calculated above.

Mass Spectrometry Identification of Protein Spots of Interest

Preparative normal and tumour tissue gels were run with a mix of 4 normal tissue samples and a mix of 4 tumour tissue samples respectively. These gels were stained with Commassie blue, spots of interest were picked and treated with Spot Handling workstation (GE Healthcare) and peptides loaded onto the MALDI-ToF target. The MS spectra were analysed with Ms-Fit software and IPI database. As indicated in Table 2, all protein spots submitted were successfully identified with an average of 13 peptides per protein, around 34% protein coverage and an error of measurement of 4.7 ppm. The 31 protein spots correspond to 22 different protein species.

Discussion

Validation of the Technology Used

The present study revealed that differentially expressed proteins between tumour and normal tissues have been identified by 2D gel electrophoresis approach. Several proteomics investigations have been already carried out to find biomarkers for CRC (Albrethsen et al. 2005; Mori et al. 2005; Ahmed, 2005; Alessandro et al., 2005; Drew et al., 2005, Alfonso et al., 2005; Friedman et al. 2004; Lawrie L C et al. 2001). Some of the proteins we found to be regulated have been already identified: Glycyl-tRNA synthetase (spot 241), 60 kDa heat shock protein (spot 543 and 543 left), Adenosylhomocysteinase (spot 768), Inorganic pyrophosphatase (spot 1015), Annexin A4 (spot 1049), F-actin capping protein beta subunit (spot 1052), Tropomyosin alpha 4 (spot 1081 and 1458), Rho GDP-dissociation inhibitor 1 (spot 1171), 14-3-3 protein alpha/beta (spot 1171), Translationally controlled tumor protein (spot 1229), and serum albumin (spot 733, 346, 364, 404, 435, 460, 462, 519, 877, 1060 and 1256). Except for the serum albumin spot 733, the regulation we observed for all these proteins is in agreement with that found previously. The fact that we identified these proteins in our study demonstrates the high value of the samples analysed and the accuracy and the sensitivity of the approach we used. On the other hand, these observations confirm the high resolution of our 2-DE protocol. Indeed, all publications dealing with the 2D electrophoresis approach (Mori et al. 2005; Alfonso et al., 2005; Friedman et al. 2004) used DIGE (Fluorescence 2-D Difference Gel Electrophoresis) Technology (GE Healthcare).

New Biomarkers for CRC

Our study identified proteins in colon cancer tissue: Transforming growth factor-beta induced protein IG-H3 (spot 407), Suppressor of G2 allele of SKP1 homolog (spot 949), Hypothetical protein (spot 975), Calponin-2 (spot 983), Heat shock protein HSP90-beta (spot 1191), Serotransferrin (spot 361), 26S proteasome subunit p40.5 (spot 877), Aldo-keto reductase family 1 member B10 (spot 943), Fructosamine-3-kinase (spot 943), Peripherin (spot 543) and Phosphoglycerate mutase 1 (spot 1354).

Because (i) this study was carried out to find new biomarkers for CRC and (ii) it is easier and more accurate to detect a higher protein expression in cancer stage than a lower one, we present now information about functions of the up-regulated proteins in cancer tissue.

Transforming growth factor-beta induced protein IG-H3 (spot 407) is a polypeptide of unknown function, expressed in the keratinocytes of the cornea (Escribano et al. 1994). The encoding gene TGFB1 was shown to be significantly elevated in colorectal cancer and adenoma (Zhang et al. 1997; Buckhaults et al. 2001).

Suppressor of G2 allele of SKP1 homolog (spot 949) may play a role in ubiquitination and proteasome degradation of target proteins. The two isoforms have been confirmed by immunoblotting (Niikura and Kitagawa, 2003).

The hypothetical protein (spot 975) has no function but the amino-acid sequence is strictly identical to the C-terminal sequence (611-922) of the URG4 protein as illustrated in FIG. 8. Overexpression of URG4 in HepG2 cells accelerated tumour development in nude mice (Tufan et al. 2002).

Calponin-2 (spot 983) is a thin filament-associated protein that is implicated in the regulation and modulation of smooth muscle contraction. It is capable of binding to actin, calmodulin, troponin C and tropomyosin. The interaction of calponin with actin inhibits the actomyosin Mg-ATPase activity (Kitching et al. 2002).

The heat shock protein HSP90-beta (spot 1191) is a molecular chaperone, constitutively expressed and guides the normal folding, intracellular disposition and proteolytic turnover of many of the key regulators of cell growth and survival. The essential guard duty of the heat shock protein HSP90 seems to offer a unique anticancer strategy of considerable promise (Whitesell et al. 2005).

Phosphoglycerate mutase 1 (spot 1354) is a glycolytic enzyme. Recently, a small molecule, MJE3, that inhibits breast cancer cell proliferation has been identified (Evans et al. 2005). MJE3 binds phosphoglycerate mutase 1 resulting in enzyme inhibition. The authors suggested that cancer cells depend on glycolysis for viability and promote phosphoglycerate mutase 1 as a potential therapeutic target.

Concluding Remarks

The aim of this study was to screen tissue and blood samples from CRC diseased patients to find new biomarkers. We used 2-DE gel electrophoresis to display proteins, silver-staining to detect protein spots and mass spectrometry to identify proteins of interest.

In this study, we presented results from the tissue analysis. The sample preparation was carried out by an experienced technician using a unique and identical protocol for all samples. They were treated at the same time. We observed that samples had different colours (more or less red/pink/brown). 2D gels from 2 tumour samples displayed an abnormal profile characteristic of samples where protein degradation occurred (absence of protein spot in the high molecular weight gel region, increased number of protein spots in the low molecular weight gel region and a thicker running front at bottom of the gel). These two samples have lowest protein concentrations as well and it was difficult to get them to a powder-like consistency.

Moreover, it is obvious that colon cells are perfused with blood where albumin represents ~50% of the protein content. Because the sample colour varies (pink/red/brown), we can imagine that they contained different amounts of albumin. This may explain why we identified albumin as regulated protein. The sample preparation is well known to be the critical step, precautions should be taken before freezing samples. For example, we can suggest to put tissue onto paper and leave them for few minutes to make sure that blood is sucked out of the tissue. This kind of precaution may prevent misinterpretation of observations.

With our 2D method, 31 protein spots were found to be differentially expressed between normal and tumour tissues. All these spots were identified by peptide mass fingerprinting (PMF) and they correspond to 22 different protein species.

Interestingly, 11 proteins (50%) we identified corresponded to new markers for CRC. 6 proteins are of particular interest because they are over-expressed in tumour tissue. The other 11 proteins (50%) we identified have been already published from biomarker discovery studies using fluorescence dyes (DIGE Technology). These 11 proteins may be considered as validation of the power of our methodology and demonstrate the high sensitivity of our silver-staining protocol. The fact that these proteins have been re-found in our investigation with another sample set confirms the value of these markers.

Example 2

Two-dimensional gel electrophoresis and mass spectrometry were used to analyse protein expression in tumour- and control plasma samples. Each sample was individually depleted and separated with 2-DE gel. We have found differences in abundance for 7 spots with statistically significant changes between tumour and control samples (spots present within at least 60% of gels, 1.5 fold down/up regulation and p value<0.005). All protein spots were identified by MALDI-ToF MS and they corresponded to 4 different protein species.

15 patients with colorectal cancer and 20 healthy controls were selected. All samples were depleted with MARS column from Agilent at the same time and proteins were TCA-precipitated.

2D Gel Electrophoresis, Image Analysis and Mass Spectrometry:

For each plasma sample, a single analytical gel was run (pH 3-10NL, 10% Acrylamide, 100 µg protein load). The gels were silver-stained, scanned and the gel images were analysed with ProGenesis software (v2006).

All 45 analytical gel images (20 healthy plasma gels for the control group and 15 tumour plasma gels for the tumour group) were introduced into the image analysis. The two groups were compared to each other. To select regulated spots, we used the following criteria: spots present within at least 60% of gels, 1.5 fold change and p value<0.005 (Mann-Whitney Test).

For the preparative gels, 5 normal samples were mixed together and 5 tumour samples were mixed together and 350 µg protein of each mix sample were loaded onto the first IPG (pH 3-10NL, 10% Acrylamide). The gels were Commassie-stained and scanned.

The protein spots of interest were picked from the preparative gels, treated with Spot Handling Workstation (GE Healthcare). The peptide profiles were generated with MALDI-ToF, analysed with Ms-Fit software (Protein Prospector) and searched against IPI database. When the cross-reference with SwissProt is available in IPI database, the reference in SwissProt is indicated (FIG. 19).

Results

1—Image Analysis Strategy and Number of Regulated Protein Spots Detected

Gel images were analysed with ProGenesis (v2006). Spot detection, matching, background subtraction and normalisation were automatically performed by ProGenesis. The background subtraction method used is the proprietary background subtraction algorithm developed by Nonlinear Dynamics. The algorithm calculated a background level based on a surface model of the entire gel. The normalisation mode used is the "Total Spot Volume" method. In this method, the volume of each spot is divided by the total volume of all of the spots in the gel. Since this method tends to produce extremely small values, the result is multiplied by a factor. For example, if you use 100 as factor, which is default value, you will produce Spot Percentage volume.

We decided that the multiplication by a factor of 1000 enables larger integers to be used in the data analyses than the default value indicated by ProGenesis. Then the spot data were exported to Excel and a macro was used to calculate Coefficient of Variation (CV in %), Student T-Test, Mann-Whitney test and Regulation factor between tumour versus normal spot volume ratio within the $99.5^{th}$ confidence level ($p<0.005$).

Based on our experience, we applied these selection criteria—spots have to be found within at least 60% of gels, 1.5-fold up/down change within the $99.5^{th}$ confidence level (Mann-Whitney test; $p<0.005$). With the prerequisite of spot presence within 60% of gels, around 650 spots went into the statistical analysis. 7 spots were found to be differentially expressed between tumour and normal plasma samples. These spots are listed in FIG. 19. 2 spots are up regulated in tumour sample group and 5 spots are down-regulated in normal sample group. The spot location in gels is indicated in FIG. 20.

2—Mass Spectrometry Identification of Protein Spots of Interest

Preparative normal- and tumour plasma gels have been run with a mix of 5 normal samples and a mix of 5 tumour samples respectively. These gels were stained with Commassie blue, spots of interest were picked and treated with Spot Handling Workstation (GE Healthcare) and peptides loaded onto the MALDI-ToF target. The MS spectra were analysed with Ms-Fit software and IPI database. As indicated in FIG. 19, all protein spots submitted were successfully identified with an average of 13 peptides per protein, around 20% protein coverage. The seven protein spots correspond to four different protein species (FIG. 19).

Discussion

1—No Protein Previously Found to be Regulated in Tissue was Found to be Regulated in Plasma In Example 1 based on the analysis of differentially expression of proteins between tumour- and normal tissues, we identified 22 different regulated proteins. Despite the fact that some of these 22 proteins have been already seen in plasma, none of them was found to be regulated in plasma.

The fact that we identified two different sets of regulated proteins, one marker set for CRC tissue samples and one marker set for plasma samples might indicate that the picture corresponding to the metabolism characteristic of cancer cells in tissue is not directly transferred into the blood stream. It could be due to the role of filter of the plasma membrane of the tissue cell and/or the high dilution rate into the blood that the 2D gel approach could not compensate. At least, in our study in tissue, we identified serum albumin as a regulated protein. This protein has been removed from the plasma (see experimental procedure above) and consequently could not be seen in plasma samples we investigated.

2—Regulated Proteins Detected in CRC Plasma

In our plasma study, we found two up regulated spots in tumour samples (spot 748; 2049) identified as SERPIN C1 protein and Haptoglobin precursor respectively and five down regulated spots in tumour plasma corresponding to 3 different proteins species alpha-2 macroglobulin (spots 707; 710; 711), Serpin C1 protein (spot 1040) and Apolipoprotein A IV (spot 1149) (FIG. 19).

SERPIN C1 protein (or Antithrombin 3) is a very important protease inhibitor in plasma that regulates the blood coagulation cascade. Recently, Sierko and coll. (2006) have observed that in most cases of colon cancer Antithrombin 3 expression has very low intensity in a few cancer foci. In approximately 15% of cases there was no AT 3 expression, while in other 15% of examined fragments of colon cancer AT 3 was readily detected. In our gels, two spots were identified as Antithrombin 3 and one spot is down regulated (1040) and one is up regulated (748). The different regulations of isoforms of the same protein in colorectal cancer serum samples have been already observed. Indeed, Rodriguez-Pineiro and coll. (2006) have identified a N-glycosylated isoform of clusterin which is up regulated in CRC samples and 15 N-glycosylated isoforms of clusterin which are down regulated or absent in CRC samples. As 4 sites known for N-glycosylation of Antithrombin are indicated in Swiss-Prot (P01008), we can imagine that similar events might happen to Antithrombin 3 explaining our observations.

Haptoglobin protein has two chains alpha and beta. A major function of haptoglobin is to bind hemoglobin (Hb) to form a stable Hp-Hb complex and thereby prevent Hb-induced oxidative tissue damage. This protein has been also found to be regulated in Alzheimer's disease samples. The spot we identified has been already identified as haptoglobin as well by another group (see note, spots are indicated in red) that confirms our identification.

Bresalier and coll. (2004) identified haptoglobin protein as being a ligand for galectin-3. Galectin-3 is a beta-galactoside-binding protein implicated in tumour progression and metastasis of colorectal cancers. They concluded that the major circulating ligand for galectin-3, which is elevated in the sera of patients with colon cancer, is a cancer-associated glycoform of haptoglobin. Immunohistochemical staining confirmed the absence of haptoglobin protein in normal colon and the ectopic expression of haptoglobin in colon cancers and adenomatous polyps.

Alpha-2-macroglobulin protein is able to inhibit all four classes of proteinases by a unique "trapping" mechanism. Alpha-2-macroglobulin together with myeloperoxidase are involved in molecular pathways leading to beta-amyloid deposition (Du et al. 1998). Alpha-2-macroglobulin can bind prostate-specific protein (PSA) and then the PSA-A2M complex is not detected by conventional PSA immunoassays (Lilja et al. 1991). Alpha-2 macroglobulin has been identified as a marker for hepatocellular carninogenesis (Kawakami et al. 2005) but not for colorectal cancer. This protein has been also found to be down regulated in Alzheimer's disease samples. The mature protein has a molecular weight of 160796 Da, which does not fit to the observed molecular weigh of the spots in gel (~100 kDa, FIG. 20, spots 707; 710; 711). We can imagine that the protein identified may correspond to a fragment of the full-length sequence of alpha-2-macroglobulin The spots we identified as alpha-2-macroglobulin belong to the same chain of spots (FIG. 20), we can also imagine that the difference between these spots may be due to a post-translational modification of the protein.

Apolipoprotein A4 is a major component of HDL (High Density Lipoprotein) and chylomicrons and required for activation of lipoprotein lipase by Apolipoprotein C2. This protein is produced in intestine and then secreted in the plasma. In our study, the apolipoprotein A4 expression is repressed in CRC patients, which correspond to the opposite expression observed in hepatocellular carcinoma (Kawakami et al. 2005) and in pancreatic cancer (Zervos et al. 2006).

Concluding Remarks

The aim of this study was to screen depleted plasma samples from CRC diseased patients to find new biomarkers. We used 2-DE gel electrophoresis to display proteins, silver-staining to detect protein spots and mass spectrometry to identify proteins of interest.

Experienced technicians have performed the plasma depletion, sample preparation and 2D gel electrophoresis. All samples were treated at the same time. Because the samples were perfectly packed and received in an excellent status, no difficulties happened during these critical steps and no degradation was observed in the 2D gels.

Seven protein spots were found to be differentially expressed between normal- and tumour plasma patients. All these spots were identified by PMF and they correspond to four different protein species.

Interestingly, one protein we identified (Haptoglobin) is already known to be associated with CRC. This may be considered as validation of our approach. The identification of the same colorectal cancer markers in different studies and groups reinforce their validity.

Moreover, the proteins preferentially expressed in healthy patients (alpha-2-macroglobulin and Apolipoprotein A IV) could be considered as surrogate markers. These markers could be measured after treatment or surgical intervention. If the proteins are newly expressed in patients, they may reflect a success of the treatment or intervention. Further investigations with a larger set of samples should be carried out to confirm our preliminary results.

REFERENCES

Ahmed F E, Expert Rev Mol Diagn 2005; 5: 353-375.
Albrethsen J, Bogebo R, et al., BMC Cancer 2005; 5: 8-17.
Alessandro R, Belluco C, et al. Clin Colorectal Cancer 2005: 4: 396-402.
Alfonso P, Nunez A, et al., Proteomics 2005; 5: 2602-2611.
Bresalier R S, Byrd J C, Tessler D, et al., Gastroenterology, 2004; 127: 741-748.
Broll R, Erdmann H, et al., Eur. J Surg Oncol 2001; 27: 37-42.
Buckaults P, Rago C, et al. Cancer Res 2001; 61: 6996-7001.
Drew J E, Rucklidge G J, et al. Biochem Biophys Res Commun 2005; 330: 81-87.
Du Y, Bales K R, Dodel R C, et al., J. Neurochem. 1998; 70: 1182-1188.
Enwegen J., Helgason H., Cats A., et al., World J. Gastroenterology 2006; 12: 1536-1544.

Escribano J, Hernando N, et al. J Cell Physiol 1994; 160: 511-521.
Evans M J, Saghatelian A, et al., Net Biotechnol 2005; 23: 1303-1307.
Fernandez-Fernandez L, Tejero E, et al., Eur. J Surg Oncol 1995; 21: 388-390.
Friedman D, Hill S, et al., Proteomics 2004; 4: 793-811.
Gold P, Freedman S O, *J. Exp. Med.* 1965; 121: 439-162.
Hammel P, Soussi T, Rev Med Interne 2000; 21: 167-173.
Kawakami T., Hoshida Y., Kanai F., et al., Proteomics, 2005; 5; 4287-4295.
Kitching R, Qi S, et al. J Bone Miner Metab 2002; 20: 269-280.
Lawrie L C, Curran S, et al. J Clin Pathol: Mol Pathol 2001; 54: 253-258.
Lilja H, Christensson A, Dahlen U, et al. Clin Chem 1991; 37:1618-1625.
Moll R, Franke W W, et al. Cell 1982; 31: 11-14.
Mori Y, Kondo T, et al. J Chromatogr B Analyt Technol Biomed Life Sci. 2005; 823: 82-97.
Niikura Y, Kitagama K, DNA Seq 2003; 14: 436-441.
Nilsson O, Johannsson C, et al. Br J Cancer 1992; 65: 215-221.
Rodriguez-Pineiro A N, Paez de la Cadena M, Lopez-Saco A, et al. Mol. Cell. Proteomics, 2006; in press.
Roessler M, Rollinger W, Mantovani-Endl L, et al. Mol. Cell. Proteomics 2006; in press.
Sierko E, Zawadzki R J, Zimnoch L, Pol. Merkuriusz Lek., 2006; 20; 462-467.
Shiota G, Ishida M, et al., Dig Dis Sci 2000; 45: 122-128.
Tufan N L, Lian Z, et al. Neoplasia 2002; 4: 355-368.
Ward D G, Suggett N, Cheng Y, et al. British J. Cancer 2006; 6: 1898-1905.
Whitesell L, Lindquist S L, Nature Rev Cancer 2005; 5: 761-772.
Yamagushi K, Enjoji M, et al., World J Gastroenterol 2005; 11: 5199-5202.
Zervos E E, Tanner S M, Osborne D A, et al. J. Surg. Res. 2006: in press.
Zhang L, Zhou W, et al. Science 1997; 276: 1268-1272.

---

The invention claimed is:

1. A method of diagnosis of colorectal cancer in a diagnostic sample of a valid body tissue taken from a human subject, comprising: subjecting the diagnostic sample to two dimensional gel electrophoresis to yield a stained gel; detecting an increased or decreased concentration of each of a plurality of differentially expressed proteins in the diagnostic sample, compared with a control, normal human sample, by detecting an increased or decreased intensity of a protein-containing spot on the stained gel, compared with a corresponding control gel, wherein detecting further comprises identifying peptide profiles for each of the plurality of proteins using a mass spectrometer, the plurality of differentially expressed proteins comprising two or more proteins selected from the group consisting of:
transforming growth factor-beta induced protein IG-H3;
suppressor of G2 allele of SKP1 homolog (isoform 2); and
hypothetical protein (part of URG4);
the plurality of proteins optionally further comprising one or more proteins selected from the group consisting of:
calponin-2;
heat shock protein HSP90-beta;
phosphoglycerate mutase 1;
serpin C1 protein; haptoglobin precursor; serotransferrin; 26S proteasome subunit p40.5;
aldo-keto reductase family 1 member B10;
fructosamine-3-kinase;
peripherin;
alpha-2-macroglobulin; and
apolipoprotein A IV.

2. A method according to claim 1, wherein the increased concentration of at least one of the plurality of differentially expressed proteins in the diagnostic sample is increased by a factor of at least 2, as compared to the control sample, or wherein the decreased concentration of at least one of the plurality of differentially expressed proteins in the diagnostic sample is decreased by a factor of at least 2, as compared to the control sample.

3. A method according to claim 1, wherein the detection is performed on the diagnostic sample by a binding assay for at least one of the plurality of differentially expressed proteins.

4. A method according to claim 3, wherein the binding assay comprises causing at least one of the plurality of differentially expressed proteins of the diagnostic sample to interact with a specific binding partner and detecting the interaction.

5. A method according to claim 4, wherein the specific binding partner is labelled.

6. A method according to claim 4, wherein the specific binding partner is an antibody or antibody fragment that recognizes at least one of the plurality of differentially expressed proteins.

7. A method according to claim 1, wherein the control sample is taken from healthy tissue of the same human subject as the diagnostic sample.

8. A method according to claim 1, wherein the control sample is taken from healthy tissue of a different human subject than the one providing the diagnostic sample.

9. A method according to claim 8, wherein the body tissue is a body fluid and the body fluid is subjected to an immunoassay.

10. A method according to claim 9, wherein the immunoassay is a western blot, enzyme-linked immunosorbent assay (ELISA), antibody microarray or bead suspension array.

11. A method according to claim 1, wherein the diagnostic sample is a tissue section that has been frozen or embedded in paraffin and which tissue section is subjected to immunohistochemistry.

12. A method according to claim 1, wherein the valid body tissue is a colorectal sample.

13. The method according to claim 1, wherein the valid body tissue is a body fluid and the body fluid is subjected to an immunoassay.

14. The method according to claim 13, wherein the immunoassay is a sandwich assay, an antibody capture assay or a competition assay.

15. A method according to claim 1, wherein the plurality of differentially expressed proteins comprises at least four proteins.

16. A method of monitoring the effect of a treatment for colorectal cancer in a subject, which comprises:
detecting a change in concentration of each of a plurality of differentially expressed proteins in a sample of a valid body tissue taken from said subject at a stage in said treatment, compared with the concentration of said each of the plurality of differentially expressed proteins in a sample of a valid body tissue taken from said subject prior to said treatment or at an earlier stage in said treatment, the plurality of differentially expressed proteins comprising at least two proteins selected from the group consisting of:
transforming growth factor-beta induced protein IG-H3;
suppressor of G2 allele of SKPI homolog (isoform 2); and
hypothetical protein (part of URG4);
the plurality of differentially expressed proteins optionally further comprising at least one protein selected from the group consisting of:
calponin-2;
heat shock protein HSP90-beta;
phosphoglycerate mutase 1;
serpin C1 protein;
haptoglobin precursor;
serotransferrin;
26S proteasome subunit p40.5;
aldo-keto reductase family 1 member B10;
fructosamine-3-kinase;
peripherin;
alpha-2-macroglobulin; and
apolipoprotein A IV,
and
wherein detecting comprises identifying peptide profiles for each of the plurality of proteins using a mass spectrometer.

17. A method according to claim 16, wherein the change in concentration is a decrease and the protein is selected from the group consisting of:
transforming growth factor-beta induced protein IG-H3;
suppressor of G2 allele of SKP1 homolog (isoform 2);
hypothetical protein (part of URG4);
calponin-2;
heat shock protein HSP90-beta;
phosphoglycerate mutase 1;
serpin C1 protein; and
haptoglobin precursor.

18. A method according to claim 16, wherein the change in protein concentration is an increase and the protein is selected from the group consisting of:
serotransferrin;
26S proteasome subunit p40.5;
aldo-keto reductase family 1 member B10;
fructosamine-3-kinase;
peripherin;
alpha-2-macroglobulin;
serpin C1 protein; and
apolipoprotein A IV.

19. A method according to claim 16, wherein the valid body tissue is colorectal tissue.

20. A method according to claim 16, wherein the valid body tissue is blood or a blood product such as serum or plasma.

21. A method according to claim 16, wherein the treatment is surgery.

22. A method according to claim 16, wherein the treatment is chemotherapy.

23. A method according to claim 16, wherein the treatment is immunotherapy.

24. A method of diagnosing colorectal cancer in a subject, the method comprising the steps of:
contacting an antibody which recognizes, binds to or has affinity for each of a plurality of differentially expressed proteins present in a sample taken from the subject, wherein the antibody is a horse-radish peroxidase labelled anti-human IgG antibody or a horse-radish peroxidase labeled anti-human IgM antibody, the plurality of proteins comprising two or more proteins selected from the group consisting of:
transforming growth factor-beta induced protein IG-H3;
suppressor of G2 allele of SKP1 homolog (isoform 2); and
hypothetical protein (part of URG4);
the plurality proteins optionally further comprising one or more proteins selected from the group consisting of:
calponin-2;
heat shock protein HSP90-beta;
phosphoglycerate mutase 1;
serpin C1 protein;
haptoglobin precursor;
serotransferrin;
26S proteasome subunit p40.5;
aldo-keto reductase family 1 member B10;
fructosamine-3-kinase;
peripherin;
alpha-2-macroglobulin; and
apolipoprotein A IV; and
detecting a change in concentration of each of the plurality of differentially expressed proteins in the sample compared with a control, normal sample, and
wherein the step of contacting comprises performing a binding assay.

25. The method according to claim 24, wherein the antibody is immobilized on a solid phase.

26. The method according to claim 24, wherein the antibody is immobilized on beads or as a chip.

27. A method of detecting a set of protein biomarkers indicative of colorectal cancer in a diagnostic sample of a valid body tissue taken from a human subject, comprising:
(a) detecting an increased concentration of the protein biomarkers in the diagnostic sample, compared with a control, normal human sample, the protein biomarkers comprising:
transforming growth factor-beta induced protein IG-H3;
suppressor of G2 allele of SKP1 homolog (isoform 2);
hypothetical protein (part of URG4);
calponin-2;
heat shock protein HSP90-beta; and
phosphoglycerate mutase 1;
wherein the step of detecting comprises subjecting the diagnostic sample to two dimensional gel electrophoresis to yield a stained gel and detecting an increased intensity of a protein-containing spot on the stained gel, compared with a corresponding control gel, wherein the step of detecting further comprises identifying peptide profiles for each of the protein biomarkers using a mass spectrometer.

28. The method of claim 27, wherein the increased concentration of each of the proteins in the diagnostic sample is increased by a factor of at least 2, as compared to the control sample.

* * * * *

SEQUENCE LISTING

<160> NUMBER OF SEQ ID NOS: 2

<210> SEQ ID NO 1
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Gln Phe Tyr Glu Ala Glu Ser Cys Leu Val Glu Ala Gly Arg
1               5                   10                  15

Leu Pro Ala Gly Gln Arg Arg Phe Ala His Phe Pro Gly Leu Ala Ser
            20                  25                  30

Glu Leu Leu Leu Thr Gly Leu Pro Leu Glu Leu Ile Asp Gly Ser Thr
        35                  40                  45

Leu Ser Met Pro Val Arg Trp Val Thr Gly Leu Leu Lys Glu Leu His
    50                  55                  60

Val Arg Leu Glu Arg Arg Ser Arg Leu Val Val Leu Ser Thr Val Gly
65                  70                  75                  80

Val Pro Gly Thr Gly Lys Ser Thr Leu Leu Asn Thr Met Phe Gly Leu
                85                  90                  95

Arg Phe Ala Thr Gly Lys Ser Cys Gly Pro Arg Gly Ala Phe Met Gln
            100                 105                 110

Leu Ile Thr Val Ala Glu Gly Phe Ser Gln Asp Leu Gly Cys Asp His
        115                 120                 125

Ile Leu Val Ile Asp Ser Gly Leu Ile Gly Ala Leu Thr Ser
    130                 135                 140

Ala Gly Asp Arg Phe Glu Leu Glu Ala Ser Leu Ala Thr Leu Leu Met
145                 150                 155                 160

Gly Leu Ser Asn Val Thr Val Ile Ser Leu Ala Glu Thr Lys Asp Ile
                165                 170                 175

Pro Ala Ala Ile Leu His Ala Phe Leu Arg Leu Glu Lys Thr Gly His
            180                 185                 190

Met Pro Asn Tyr Gln Phe Val Tyr Gln Asn Leu His Asp Val Ser Val
        195                 200                 205

```
Pro Gly Pro Arg Pro Arg Asp Lys Arg Gln Leu Leu Asp Pro Pro Gly
    210                 215                 220
Asp Leu Ser Arg Ala Ala Ala Gln Met Glu Lys Gln Gly Asp Gly Phe
225                 230                 235                 240
Arg Ala Leu Ala Gly Leu Ala Phe Cys Asp Pro Glu Lys Gln His Ile
                245                 250                 255
Trp His Ile Pro Gly Leu Trp His Gly Ala Pro Pro Met Ala Ala Val
            260                 265                 270
Ser Leu Ala Tyr Ser Glu Ala Ile Phe Glu Leu Lys Arg Cys Leu Leu
            275                 280                 285
Glu Asn Ile Arg Asn Gly Leu Ser Asn Gln Asn Lys Asn Ile Gln Gln
290                 295                 300
Leu Ile Glu Leu Val Arg Arg Leu
305                 310

<210> SEQ ID NO 2
<211> LENGTH: 322
<212> TYPE: PRT
<213> ORGANISM: Homo sapiens

<400> SEQUENCE: 2

Pro Leu Gly Val Glu His Phe Leu Arg Glu Met Gly Gln Phe Tyr Glu
1               5                   10                  15
Ala Glu Ser Cys Leu Val Glu Ala Gly Arg Leu Pro Ala Gly Gln Arg
                20                  25                  30
Arg Phe Ala His Phe Pro Gly Leu Ala Ser Glu Leu Leu Leu Thr Gly
            35                  40                  45
Leu Pro Leu Glu Leu Ile Asp Gly Ser Thr Leu Ser Met Pro Val Arg
50                  55                  60
Trp Val Thr Gly Leu Leu Lys Glu Leu His Val Arg Leu Glu Arg Arg
65                  70                  75                  80
Ser Arg Leu Val Val Leu Ser Thr Val Gly Val Pro Gly Thr Gly Lys
                85                  90                  95
Ser Thr Leu Leu Asn Thr Met Phe Gly Leu Arg Phe Ala Thr Gly Lys
                100                 105                 110
Ser Cys Gly Pro Arg Gly Ala Phe Met Gln Leu Ile Thr Val Ala Glu
            115                 120                 125
Gly Phe Ser Gln Asp Leu Gly Cys Asp His Ile Leu Val Ile Asp Ser
        130                 135                 140
Gly Gly Leu Ile Gly Gly Ala Leu Thr Ser Ala Gly Asp Arg Phe Glu
145                 150                 155                 160
Leu Glu Ala Ser Leu Ala Thr Leu Leu Met Gly Leu Ser Asn Val Thr
                165                 170                 175
Val Ile Ser Leu Ala Glu Thr Lys Asp Ile Pro Ala Ala Ile Leu His
                180                 185                 190
Ala Phe Leu Arg Leu Glu Lys Thr Gly His Met Pro Asn Tyr Gln Phe
            195                 200                 205
Val Tyr Gln Asn Leu His Asp Val Ser Val Pro Gly Pro Arg Pro Arg
210                 215                 220
Asp Lys Arg Gln Leu Leu Asp Pro Pro Gly Asp Leu Ser Arg Ala Ala
225                 230                 235                 240
Ala Gln Met Glu Lys Gln Gly Asp Gly Phe Arg Ala Leu Ala Gly Leu
                245                 250                 255
Ala Phe Cys Asp Pro Glu Lys Gln His Ile Trp His Ile Pro Gly Leu
            260                 265                 270
```

-continued

```
Trp His Gly Ala Pro Pro Met Ala Ala Val Ser Leu Ala Tyr Ser Glu
        275                 280                 285

Ala Ile Phe Glu Leu Lys Arg Cys Leu Leu Glu Asn Ile Arg Asn Gly
    290                 295                 300

Leu Ser Asn Gln Asn Lys Asn Ile Gln Gln Leu Ile Glu Leu Val Arg
305                 310                 315                 320

Arg Leu
```